(12) United States Patent
Park et al.

(10) Patent No.: US 9,877,946 B2
(45) Date of Patent: *Jan. 30, 2018

(54) METHOD FOR TREATING, MANAGING, INHIBITING, OR PREVENTING OBESITY

(71) Applicants: RESEARCH & BUSINESS FOUNDATION SUNGKYUNKWAN UNIVERSITY, Suwon-si (KR); GYEONGGI INSTITUTE OF SCIENCE & TECHNOLOGY PROMOTION, Suwon-si (KR)

(72) Inventors: Kye Won Park, Suwon-si (KR); Nojoon Song, Suwon-si (KR); Suk Chan Lee, Suwon-si (KR); Jin-Mo Ku, Suwon-si (KR)

(73) Assignees: Research & Business Foundation Sungkyunkwan University, Suwon-si (KR); GYEONGGIDO BUSINESS & SCIENCE ACCELERATOR, Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/374,187

(22) Filed: Dec. 9, 2016

(65) Prior Publication Data

US 2017/0087126 A1  Mar. 30, 2017

Related U.S. Application Data

(63) Continuation of application No. 14/745,772, filed on Jun. 22, 2015, now Pat. No. 9,549,908.

(30) Foreign Application Priority Data

Jun. 25, 2014  (KR) .................. 10-2014-0078275
May 22, 2015  (KR) .................. 10-2015-0071581

(51) Int. Cl.
*A61K 31/35* (2006.01)
*A61K 31/12* (2006.01)
*A61K 31/353* (2006.01)
*C07D 311/32* (2006.01)
*C12N 5/077* (2010.01)

(52) U.S. Cl.
CPC ............ *A61K 31/353* (2013.01); *A61K 31/12* (2013.01); *C07D 311/32* (2013.01); *C12N 5/0653* (2013.01); *C12N 2501/999* (2013.01); *C12N 2506/1384* (2013.01)

(58) Field of Classification Search
CPC ................................ A61K 31/35; A61K 31/12
USPC ..................................................... 514/456, 678
See application file for complete search history.

(56) References Cited

U.S. PATENT DOCUMENTS 9,549,908 B2 *  1/2017  Park ................... A61K 31/12
2004/0014721 A1  1/2004  Hensley et al.

FOREIGN PATENT DOCUMENTS

KR  10-2010-0114579 A   10/2011
KR  10-2012-0049214 A    5/2012
WO  WO 2013/149258 A2   10/2013

OTHER PUBLICATIONS

Song, No-Joon, et al. "Butein Is a Novel Anti-Adipogenic Compound." Journal of lipid research 54.5 (2013): 1385-1396. (12 pages in English).
Wang, Zheng, et al. "Inhibition of Adipocyte Inflammation and Macrophage Chemotaxis by Butein." European journal of pharmacology 738 (2014): (9 pages in English).

* cited by examiner

*Primary Examiner* — Raymond J Henley, III
(74) *Attorney, Agent, or Firm* — NSIP Law

(57) ABSTRACT

A composition for inducing differentiation into beige adipocytes from white adipocytes, including butein, a butein derivative, or a pharmaceutically available salt thereof as an active ingredient, and a method of inducing the differentiation are provided. Increases in expressions of UCP-1 and PRDM4 are confirmed using the active ingredient, that is, the butein or butein derivative, and therefore the composition is expected to be used in preventing or treating obesity, and more basically, for target treatment.

18 Claims, 17 Drawing Sheets

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: PRDM4 siRNA_sense 1

<400> SEQUENCE: 1
gaauuacgcu caacagauau u                                               21
```

```
<210> SEQ ID NO 2
<211> LENGTH: 21
<212> TYPE: RNA
<213> ORGANISM: Artificial Sequence
<220> FEATURE:
<223> OTHER INFORMATION: PRDM4 siRNA_sense 2

<400> SEQUENCE: 2
gaaagugagc ugcuuuucuu u                                              21
```

METHOD FOR TREATING, MANAGING, INHIBITING, OR PREVENTING OBESITY

CROSS-REFERENCE TO RELATED APPLICATION

This application is a continuation of U.S. patent application Ser. No. 14/745,772 filed on Jun. 22, 2015,(now U.S. Pat. No. 9,549,908), which claims priority to and the benefit of Korean Patent Application No. 10-2014-0078275, filed on Jun. 25, 2014, and 10-2015-0071581, filed on May 22, 2015, the disclosure of which is incorporated herein by reference in its entirety.

The present invention was undertaken with the support of Lead optimization of brown fat inducing compounds No. 2016M3A9B6903450 grant funded by the Ministry of Science, ICT and Future Planning.

BACKGROUND

1. Field of the Invention

The present invention relates to a composition for inducing brown adipocytes and inducing differentiation into beige adipocytes from white adipocytes, the composition including butein, a butein derivative or a pharmaceutically available salt thereof as an active ingredient, and a method of inducing the differentiation.

2. Discussion of Related Art

Obesity is triggered by hypertrophy of subcutaneous adipose tissues caused by accumulation of excessive energy as fats in a body when imbalance in a metabolic process occurs due to endocrinal, genetic and social environmental factors. The hypertrophy of the adipose tissues is a phenomenon in which sizes or numbers of adipocytes increase (hypertrophy or hypergenesis of the adipocytes), and may have an influence on retention of a local vein-lymph system, thereby causing a vascular tissue disease in dermis-subcutaneous tissues. Therefore, the obesity is recognized as an independent disease by definition, and World Health Organization deals with the obesity as a world-wide nutritional problem and recognizes it as a disease to be treated, not only a simple dangerous factor that ruins a health.

Neutral fats excessively accumulated in obese patients are stored in a liver or muscles, as well as adipose tissues, and thus induce insulin resistance. Accordingly, consumption of the excessively-stored neutral fats may result in preventing and treating obesity and metabolic diseases caused thereby. The adipocytes are largely classified into white adipocytes, brown adipocytes and beige adipocytes. The white adipocytes are stored in a large fat globule of the neutral fat, usually found in an abdominal cavity in large numbers, and known to have a negative influence on health. It is reported that the brown adipocytes contain a larger number of mitochondria and smaller fat globules than the white adipocytes, and may be induced by maintenance of a body temperature through heat generation and a proper exercise. Mice induced to contain a large number of brown adipocytes relatively induce a decrease in body weight and an increase in calorie burning with respect to obesity caused by high fat diet (HFD), and thus show an effect on obesity and metabolic diseases. In addition, it is known that uncoupling protein-1 (UCP-1) is expressed on a high level from the brown adipocytes, and plays a critical role in generating heat in the form of calorie burning, not calorie storage, in adipocytes. In addition to the brown adipocytes, beige adipocytes are also recognized as important adipocytes. The beige adipocytes are induced from white adipocytes that are harmful to health by an exercise or stimulation such as a cold, and have lower phenotypes of the white adipocytes, but have characteristics of the brown adipocytes, leading to an increase in expression of UCP-1. It is known that the beige adipocytes are also helpful for obesity and metabolic diseases, similar to the brown adipocytes found in mice. In addition, most of the helpful brown adipocytes found in humans are known as beige adipocytes, and thus concerns on conversion of or induction of differentiation of the white adipocytes harmful to health into the beige adipocytes relatively helpful for health are increasing.

Therefore, regulation of activity of UCP-1 and genesis of beige (or brown) adipocytes are becoming main subjects for studies, and the studies on this have been being executed (Korean Patent Publication No. 10-2012-0049214), but these are still inadequate.

SUMMARY OF THE INVENTION

The present invention is directed to a composition for inducing brown adipocytes and inducing differentiation into beige adipocytes from white adipocytes, which includes butein, a butein derivative or a pharmaceutically available salt thereof as an active ingredient.

The present invention is also directed to a method of inducing differentiation into beige adipocytes from white adipocytes, which includes treating the white adipocytes with butein, a butein derivative or a pharmaceutically available salt thereof.

The present invention is also directed to a method of screening an obesity treating material, which includes: a) treating adipocytes with a obesity treating candidate material in vitro; b) measuring expression of a PRDM4 gene of the adipocyte; and c) selecting a material for improving the expression of the PRDM4 gene as an obesity treating material, compared to a non-treatment group.

However, technical objects to be achieved by the present invention are not limited to the above-described objects, and other objects which is not be described will be clearly understood to those of ordinary skill in the art from the following descriptions.

According to an aspect of the present invention, there is provided a composition for inducing differentiation into beige adipocytes from white adipocytes, which includes butein, a butein derivative, or a pharmaceutically available salt thereof as an active ingredient.

In one exemplary embodiment of the present invention, the butein derivative may be a compound represented by Formula 1:

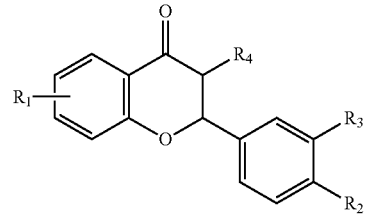

[Formula 1]

In Formula 1, $R_1$ may be hydrogen, halogen, linear or branched C1-C6 alkyl, linear or branched C2-C6 alkenyl, linear or branched C2-C6 alkynyl, OH, $OR_5$, or $O(CO)R_5$, in which $R_5$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, $R_2$ and $R_3$ may be identical to or different from each other, each being hydrogen, halogen, linear or branched C1-C6 alkyl, linear or branched C2-C6 alkenyl, linear or branched C2-C6 alkynyl, OH, $OR_6$, or $O(CO)R_6$, in which $R_6$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, and $R_4$ may be hydrogen or linear or branched C1-C6 alkyl.

In another exemplary embodiment of the present invention, the butein derivative may be a compound represented by Formula 2.

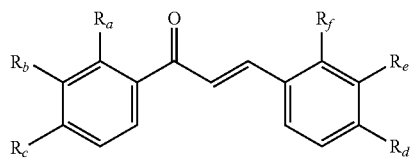

[Formula 2]

In Formula 2, $R_a$, $R_b$, and $R_c$ may be identical to or different from each other, each being hydrogen, halogen, linear or branched C1-C6 alkyl, linear or branched C2-C6 alkenyl, linear or branched C2-C6 alkynyl, OH, $OR_g$, or $O(CO)R_g$, in which $R_g$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, $R_d$, $R_e$, and $R_f$ may be identical to or different from each other, each being hydrogen, halogen, linear or branched C1-C6 alkyl, linear or branched C2-C6 alkenyl, linear or branched C2-C6 alkynyl, OH, $OR_h$, or $O(CO)R_h$, in which $R_h$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S.

In still another exemplary embodiment of the present invention, the butein derivative may be 2-(3,4-dihydroxyphenyl)-7-hydroxychroman-4-one; (E)-1-(2,4-dihydroxyphenyl)-3-(4-hydroxy-3-methoxyphenyl)prop-2-en-1-one; 7-hydroxy-2-(4-hydroxy-3 -methoxyphenyl)chroman-4-one; (E)-1-(2,4-dihydroxyphenyl)-3-(3-hydroxy-4-methoxyphenyl)prop-2-en-1-one; 7-hydroxy-2-(3-hydroxy-4-methoxyphenyl)chroman-4-one; (E)-1-(2,4-dihydroxyphenyl)-3-(3-fluoro-4-hydroxyphenyl)prop-2-en-1-one; (E)-1-(2,4-dihydroxyphenyl)-3-(4-hydroxyphenyl)prop-2-en-1-one; 2-(3,4-dihydroxyphenyl)-7-hydroxy-3-methylchroman-4-one; 2-(4-fluoro-3-methoxyphenyl)-7-hydroxychroman-4-one; (E)-3-(3,4-dihydroxyphenyl)-1-(4-hydroxyphenyl)prop-2-en-1-one; (E)-1,3-bis(3,4-dihydroxyphenyl)prop-2-en-1-one; (E)-1,3-bis(4-hydroxyphenyl)prop-2-en-1-one; (E)-1-(2-hydroxyphenyl)-3-(4-hydroxyphenyl)prop-2-en-1-one; (E)-3-(2,4-dimethoxyphenyl)-1-(4-hydroxyphenyl)prop-2-en-1-one; (E)-3-(2,4-dihydroxyphenyl)-1-(4-hydroxyphenyl)prop-2-en-1-one, or (E)-3-(4-hydroxy-2-methoxyphenyl)-1-(4-hydroxyphenyl)prop-2-en-1-one.

In yet another exemplary embodiment of the present invention, the butein or butein derivative may increase an activity of brown adipocytes.

In yet another exemplary embodiment of the present invention, the butein or butein derivative may increase expression of UCP-1.

In yet another exemplary embodiment of the present invention, the butein or butein derivative may increase expression of a PRDM4 gene.

According to an aspect of the present invention, there is provided a method of inducing differentiation into beige adipocytes from white adipocytes, which includes treating the white adipocytes with butein, a butein derivative or a pharmaceutically available salt thereof.

In one exemplary embodiment of the present invention, the inducing method may increase an activity of brown adipocytes.

According to an aspect of the present invention, there is provided a method of screening an obesity treating material, which includes: a) treating adipocytes with an obesity treating candidate material in vitro; b) measuring expression of a PRDM4 gene of the adipocyte; and c) selecting a material for improving the expression of the PRDM4 gene as the obesity treating material, compared to an non-treatment group.

According to an aspect of the present invention, there is provided a method of treating obesity, which includes administering a composition for inducing differentiation into an individual.

According to an aspect of the present invention, there is provided a use of a composition for treating obesity, the composition including butein, a butein derivative or a pharmaceutically available salt thereof as an active ingredient.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
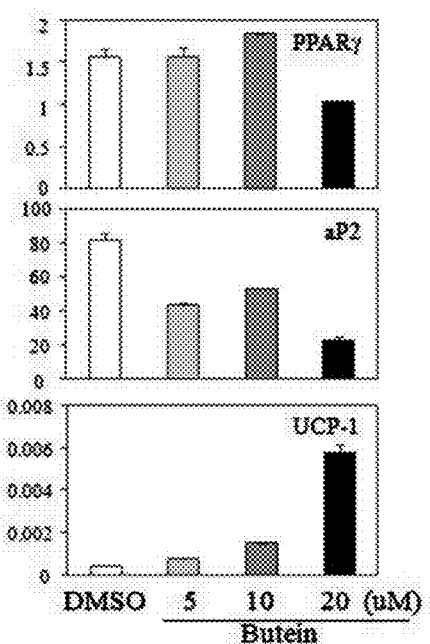
FIG. 1 shows changes in expression levels of PPARγ, aP2 and UCP-1 when C3H10T1/2 cells are induced to adipocytes and treated with butein.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

In the present invention, when butein was treated, an increase in expression of a beige adipocyte marker such as UCP-1 in a C3H101/2 cell line and increases in expressions of brown adipocyte markers such as UCP-1, PRDM16 and Cidea in T37i cells were shown. A decrease in body weight and improvements in glucose-insulin metabolism by butein treatment were also shown in HFD obesity-induced mice, and therefore the present invention was completed.

Hereinafter, the present invention will be described in detail.

In one aspect of the present invention, the present invention provides a composition for inducing differentiation into beige adipocytes from white adipocytes, which includes butein, a butein derivative or a pharmaceutically available salt thereof as an active ingredient.

In the present invention, the butein derivative is a compound represented by Formula 1:

[Formula 1]

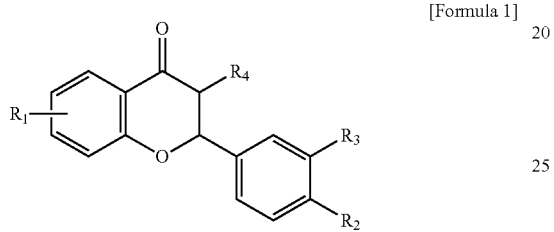

In Formula 1, $R_1$ may be hydrogen, halogen, linear or branched C1-C6 alkyl, linear or branched C2-C6 alkenyl, linear or branched C2-C6 alkynyl, OH, $OR_5$, or $O(CO)R_5$, in which $R_5$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, $R_2$ and $R_3$ may be identical to or different from each other, each being hydrogen, halogen, linear or branched C1-C6 alkyl, linear or branched C2-C6 alkenyl, linear or branched C2-C6 alkynyl, OH, $OR_6$, or $O(CO) R_6$, in which $R_6$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, and $R_4$ may be hydrogen or linear or branched C1-C6 alkyl.

as shown in Reaction Formula 1, similar to Formula 1 and the compound of Formula A may be prepared by reacting Compound C with Compound D in the presence of a proline catalyst.

[Reaction Formula 1]

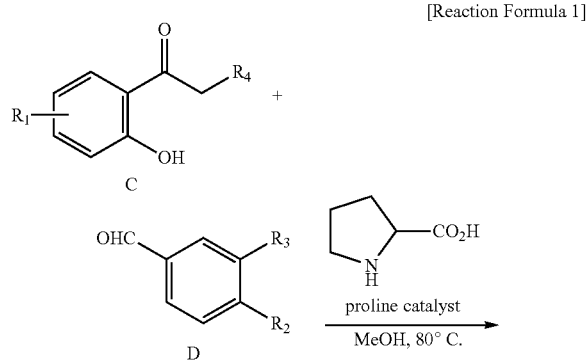

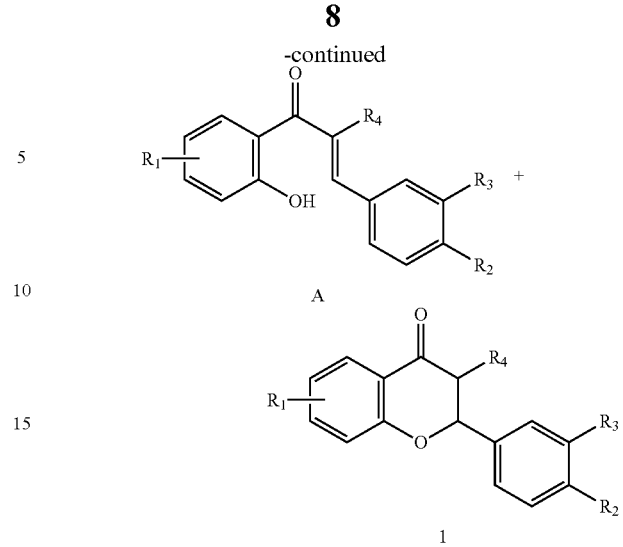

In addition, in the present invention, the butein derivative is a compound represented by Formula 2:

[Formula 2]

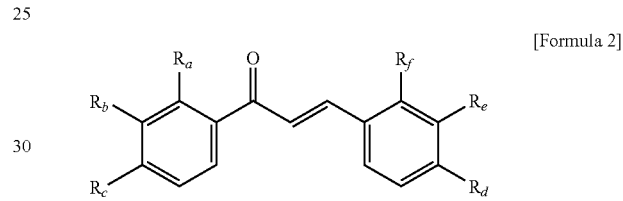

In Formula 2, $R_a$, $R_b$, and $R_c$ may be identical to or different from each other, each being hydrogen, halogen, linear or branched C1-C6 alkyl, linear or branched C2-C6 alkenyl, linear or branched C2-C6 alkynyl, OH, $OR_g$, or $O(CO) R_g$, in which $R_g$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, $R_d$, $R_e$, and $R_f$ may be identical to or different from each other, each being hydrogen, halogen, linear or branched C1-C6 alkyl, linear or branched C2-C6 alkenyl, linear or branched C2-C6 alkynyl, OH, $OR_h$, or $O(CO)R_h$, in which $R_h$ may be linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S.

as shown in Reaction Formula 2, the compound of Formula 2 may be prepared by reacting Compound E with Compound F in the presence of a base catalyst.

[Reaction Formula 2]

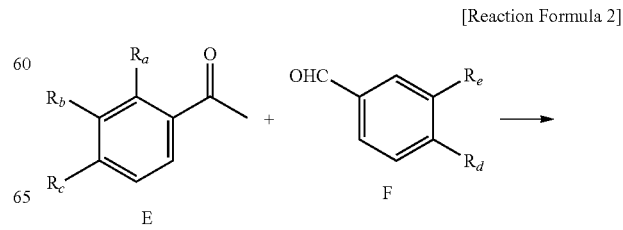

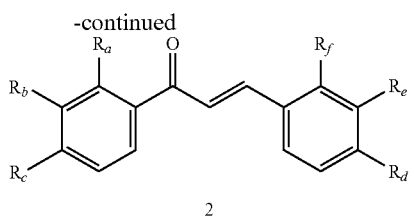

2

Particularly, the compound of Formula 1 or 2 may be, but is not limited to, selected from the group consisting of 2-(3,4-dihydroxyphenyl)-7-hydroxychroman-4-one; (E)-1-(2,4-dihydroxyphenyl)-3-(4-hydroxy-3-methoxyphenyl)prop-2-en-1-one; 7-hydroxy-2-(4-hydroxy-3-methoxyphenyl)chroman-4-one; (E)-1-(2,4-dihydroxyphenyl)-3-(3-hydroxy-4-methoxyphenyl)prop-2-en-1-one; 7-hydroxy-2-(3-hydroxy-4-methoxyphenyl)chroman-4-one; (E)-1-(2,4-dihydroxyphenyl)-3-(3-fluoro-4-hydroxyphenyl)prop-2-en-1-one; (E)-1-(2,4-dihydroxyphenyl)-3-(4-hydroxyphenyl)prop-2-en-1-one; 2-(3,4-dihydroxyphenyl)-7-hydroxy-3-methylchroman-4-one; 2-(4-fluoro-3-methoxyphenyl)-7-hydroxychroman-4-one; (E)-3-(3,4-dihydroxyphenyl)-1-(4-hydroxyphenyl)prop-2-en-1-one; (E)-1,3-bis(3,4-dihydroxyphenyl)prop-2-en-1-one; (E)-1,3-bis(4-hydroxyphenyl)prop-2-en-1-one; (E)-1-(2-hydroxyphenyl)-3-(4-hydroxyphenyl)prop-2-en-1-one; (E)-3-(2,4-dimethoxyphenyl)-1-(4-hydroxyphenyl)prop-2-en-1-one; (E)-3-(2,4-dihydroxyphenyl)-1-(4-hydroxyphenyl)prop-2-en-1-one, and (E)-3-(4-hydroxy-2-methoxyphenyl)-1-(4-hydroxyphenyl)prop-2-en-1-one.

The term "pharmaceutically available salt thereof" used herein may be prepared by a conventional method in the art, and for example, means that formation of a salt with an inorganic acid such as hydrochloric acid, hydrogen bromide, sulfuric acid, sodium hydrogen sulfate, phosphoric acid or carbonic acid or an organic acid such as formic acid, acetic acid, oxalic acid, benzoic acid, citric acid, tartaric acid, gluconic acid, seutiseu acid, fumaric acid, lactobionic acid, salicylic acid or acetylsalicylic acid (aspirin) and a pharmaceutically available salt thereof, or formation of a metal salt by a reaction with an alkali metal ion such as sodium or potassium, or formation of another type of pharmaceutically available salt by a reaction with an ammonium ion.

The term "white adipocyte" used herein is a cell having a function of accumulating large amounts of fat energy as neutral fat in a body, is intensively proliferated in the late stage of pregnancy, an infant stage and an adolescent stage and swollen 15 times, and becomes a cause of fat hypertrophy, and generally, the "adipocyte" refers to a white adipocyte.

The term "beige adipocyte" used herein may originate from a white adipose tissue, and a beige cell in which iron is present in mitochondria. Compared to the white adipocyte, the brown adipocyte is an adipocyte capable of generating heat by consuming energy, has a function of converting fat of a beige adipocyte into energy, and produces UCP-1 in response to a low temperature or a specific hormone.

The term "differentiation" used herein refers to a phenomenon in which a structure or function of cells is specialized while the cells are divided, proliferated, and then grown, that is, a change in a shape or function of cells or tissues of an organism to perform a work given thereto. Generally, the differentiation is a phenomenon of dividing a system into at least two subsystems having different properties. For example, the differentiation refers to a state in which qualitative differences are generated between parts of a biological system, which have almost the same properties from the beginning, for example, parts of an egg which have the same properties from the beginning of ontogeny give rise to distinction between a head and a body or there is a qualitative difference, like distinction between a muscle cell and a nerve cell, or as a result, the biological system is divided into qualitatively distinguishable parts or subsystems.

The composition of the present invention increases an activity of brown adipocytes, or increases the expression of UCP-1 or PRDM4.

The term "brown adipocyte" used herein is a cell having a function of converting fat into energy like the beige adipocyte, and looks yellowish brown or reddish brown with the naked eye. As the number of the brown adipocytes increase, body fat is reduced, and as a human grows old, the number of brown adipocytes decrease. While the brown adipocytes are generated in stem cells differentiating into muscle cells, the beige adipocytes are generated in a white adipocyte layer.

The term "differentiation-inducing composition" used herein refers to a composition which can induce a process by which cells in an early stage have properties as different tissues, and according to a purpose of the present invention, the composition refers to a composition which can induce differentiation into beige adipocytes from white adipocytes.

The composition for inducing differentiation into beige adipocytes of the present invention may contain butein or a butein derivative in an amount of 0.0001 to 10 wt %, and preferably, 0.001 to 1 wt % with respect to a total weight of the composition, but the present invention is not limited thereto.

In one exemplary embodiment of the present invention, an increase in expression of a beige adipocyte marker, UCP-1, caused by butein treatment was confirmed (refer to Example 1), and increases in expressions of brown adipocyte markers, PRDM16 and Cidea were confirmed (refer to Example 2). In addition, compared to other anti-obesity bioactive ingredients, it was confirmed that the composition of the present invention showed a remarkable effect on expression of UCP-1 by butein treatment (refer to Example 3), and increases in numbers of beige or brown adipocytes and an obesity improvement effect were shown in an in vivo test and HFD obesity-induced mice (refer to Examples 4 and 5). In another exemplary embodiment of the present invention, as a gene inducing bioactivity of butein, PRDM4 was found, and an increase in body weight by inhibition of PRDM4 expression and inhibition of a glucose-insulin metabolism were confirmed (refer to Examples 6 and 7). Moreover, a butein derivative was prepared, and expression levels of UCP-1 and PRDM4 were increased by treatment of the butein derivative, and therefore, it was confirmed that the composition for inducing differentiation into beige adipocytes of the present invention can be used as a pharmaceutical composition for preventing or treating obesity (refer to Examples 8 and 9).

A disease to be prevented or treated by the composition of the present invention, that is, "obesity" refers to a state in which adipocytes are proliferated and differentiated in a body due to a metabolic disorder, and therefore, fat is excessively accumulated, and when an amount of absorbing energy is relatively higher than an amount of consumption, the number and volume of the adipocytes increase, and thus a mass of a adipose tissue increases. In a cellular level, obesity means an increase in numbers and volume of adipocytes due to stimulation of proliferation and differentiation of the adipocytes.

The composition of the present invention may include a pharmaceutically available carrier. The pharmaceutically available carrier may include a saline solution, polyethyleneglycol, ethanol, vegetable oil and isopropyl myristate, but the present invention is not limited thereto. In addition, the pharmaceutically available carrier may further include a conventionally-known medium for culturing stem cells and a differentiation inducer.

The composition of the present invention may be prepared as an aqueous solution for parenteral treatment, and may preferably use a buffer solution such as a Hank's solution, a Ringer's solution or a physically buffered saline. In an aqueous injection suspension, a substrate capable of increasing viscosity of the suspension such as sodium carboxymethyl cellulose, sorbitol or dextran may be added.

In addition, a preferable form of the composition of the present invention may be a preparation for sterile injection of a water- or oil-based suspension. The suspension may be formulated according to a technique known in the art using a suitable dispersant or wetting agent (e.g., Tween 80) and a suspending agent. The preparation for sterile injection may also be a sterile injection solution or suspension in a non-toxic parenterally-available diluent or solvent (e.g., a solution in 1,3-butanediol). As a vehicle and solvent which can be used in the present invention, mannitol, water, a Ringer's solution and an isotropic sodium chloride solution may be used. In addition, a sterile non-volatile oil is conventionally used as a solvent or suspending medium. To this end, any one of less irritant non-volatile oils including synthetic mono and diglycerides may be used.

In another aspect of the preset invention, the present invention provides a method of inducing differentiation into beige adipocytes from white adipocytes, which includes treating the white adipocytes with butein, a butein derivative or a pharmaceutically available salt thereof. The method of the present invention includes administering the composition for inducing differentiation into an individual, and the "individual" used herein refers to a subject that has a disease to be treated, and specifically, a human, or a non-human mammal such as a primate, a mouse, a rat, a dog, a cat, a horse or a cow.

In still another aspect of the present invention, the present invention provides a method of screening an obesity treating material, which includes a) treating adipocytes with an obesity-treating candidate material in vitro, b) measuring expression of a PRDM4 gene of the adipocyte, and c) selecting a material for improving the expression of the PRDM4 gene as the obesity treating material, compared to a non-treatment group.

Hereinafter, exemplary examples are provided to help in understanding the present invention. However, the following examples are merely provided to more easily understand the present invention, not to limit the scope of the present invention.

EXAMPLE 1

Confirmation of Induction of Differentiation into Beige Adipocytes by Butein

To confirm induction of differentiation into beige adipocytes by butein treatment, a pluripotent stem cell line, that is, a C3H10T1/2 cell line, originating from mouse embryonic fibroblast (MEF) cells was used. The C3H10T1/2 cell line was cultured in a 6-well plate using a medium containing 1 μM dexamethasone, 5 μg/ml insulin, 20 nM 3-isobutyl-1-methylxanthine (IBMX) and PPARγ ligand (GW7845) to induce differentiation into adipocytes to a concentration of $2.5 \times 10^4$/ml for approximately 7 to 10 days. The differentiation-induced adipocytes were treated with butein for 24 hours by concentrations (5, 10 and 20 μM), and the expression of UCP-1 found in the beige adipocytes was confirmed through real-time PCR.

As shown in FIG. 1, as the concentration of butein increased, the expression of UCP-1 increased, and therefore, it was confirmed that the differentiation into beige adipocytes increased.

EXAMPLE 2

Confirmation of Increase in Number of Brown Adipocytes by Butein

To confirm an increase in number of brown adipocytes by butein treatment, brown fat precursor cells, T37i cells, were used. The T37i cells were cultured in a medium containing 5 μg/ml insulin and 1 nM triiodothyronine (T3) for 2 days, and then the differentiation into adipocytes using a medium containing 5 μg/ml insulin was induced for 6 to 8 days. The differentiation-induced adipocytes were treated with butein for 6 days by concentrations (5, 10 and 20 μM) and stained with Oil Red O, and then mRNA expression levels of PPARγ and aP2 related to the adipocyte differentiation and brown adipocyte markers, that is, UCP-1, PRDM16 and Cidea genes, were confirmed through real-time PCR.

Figure 2:
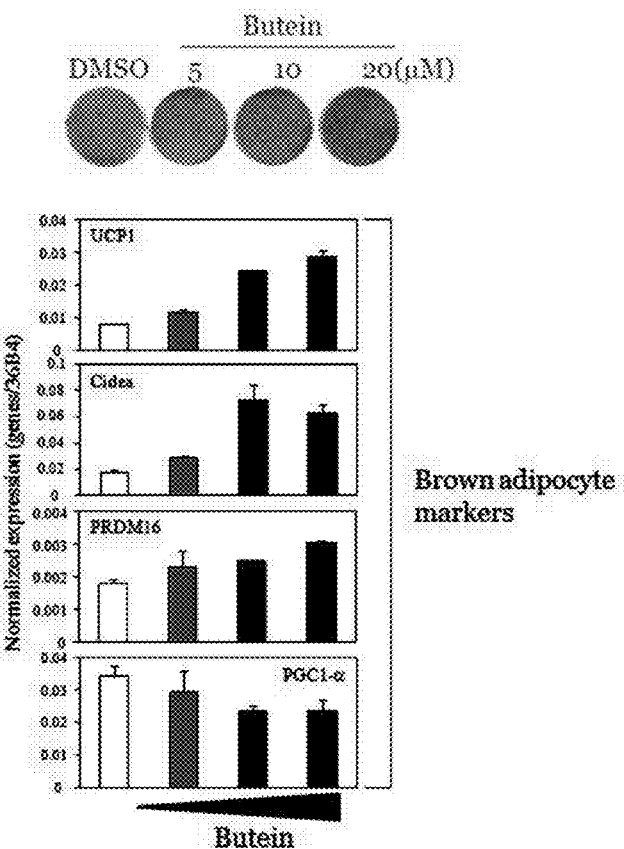
FIG. 2 shows comparison of Oil Red O staining results and mRNA expression levels of UCP-1, PRDM16, Cidea and PGC-1a through real-time PCR when T37i cells are differentiating into brown adipocytes and treated with butein.

As shown in FIG. 2, it was confirmed that, as the concentration of butein increased, the expression of UCP-1 and the expressions of the brown adipocyte markers, that is, PRDM16 and Cidea increased.

EXAMPLE 3

Confirmation of Increase in Expression of UCP-1 Specific to Butein

An increase in expression level of UCP-1 by butein treatment in C3H10T1/2 cells was compared to those by treatment of sulfuretin, fisetin, resveratrol and genistein, which are known as materials having an influence on adipocytes, and the increase in expression level of UCP-1 by butein treatment in MEF cells was compared to a DMSO-treated group as a control.

In addition, the expression levels of UCP-1 after differentiated C3H10T1/2 cells were treated with various anti-obesity bioactive materials and natural substance-derived single materials reported to have an anti-obesity effect for 24 hours were compared to that treated with butein.

Figure 3:
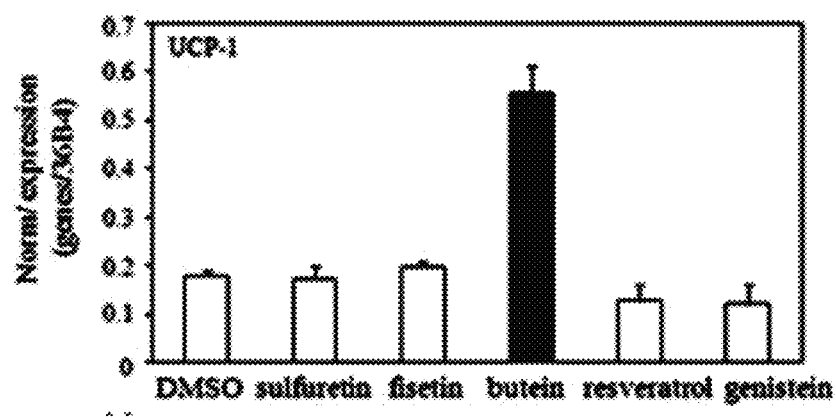
FIG. 3 shows an UCP-1 expression level when C3H10T1/2 cells are differentiating into adipocytes and treated with sulfur-tin, fisetin, butein, resveratrol or genistein.
Figure 4:
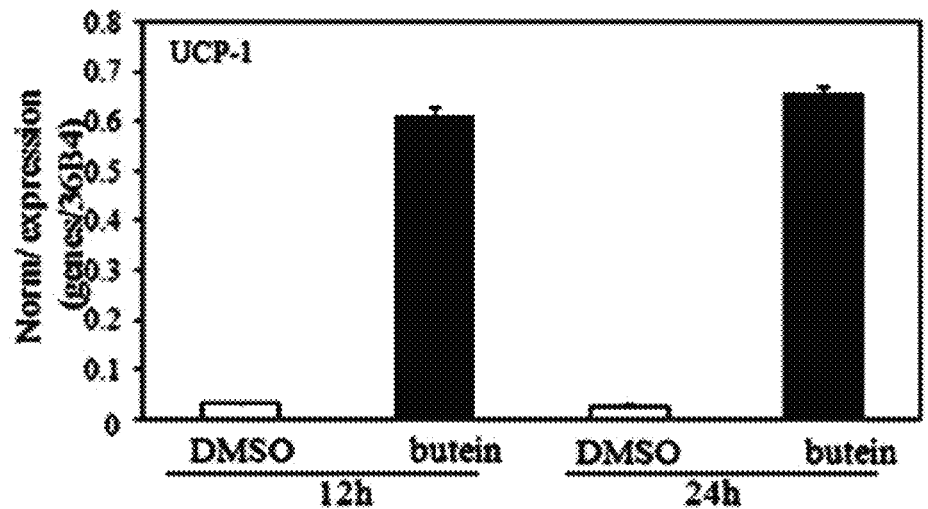
FIG. 4 shows an UCP-1 expression level when mouse embryonic fibroblast (MEF) cells are treated with butein.
Figure 5:
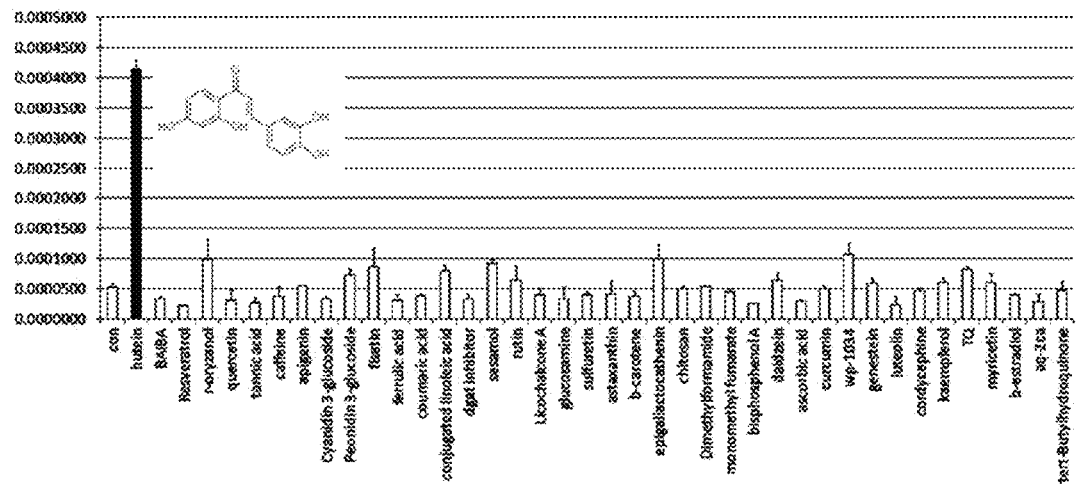
FIG. 5 shows comparison of UCP-1 expression levels between when C3H10T1/2 cells are treated with various anti-obesity bioactive materials and natural substance-derived single materials whose anti-obesity effect has been reported for 24 hours and when C3H10T1/2 cells are treated with butein.

As shown in FIGS. 3 and 4, when the C3H10T1/2 cells were treated with butein, compared to those treated with sulfuretin, fisetin, resveratrol and genistein, the expression of UCP-1 increased more than three times, and when MEF cells were treated with butein, compared to the control, the expression of UCP-1 increased more than 10 times. In addition, as shown in FIG. 5, generally, when conventionally known anti-obesity bioactive materials were treated, the expression levels of UCP-1 did not increase, but when butein was treated, the expression level of UCP-1 specifically and considerably increased.

EXAMPLE 4

Confirmation of Inhibition of White Adipocytes and Increase in Numbers of Beige and Brown Adipocytes In Vivo To examine activities of butein to increase the numbers of beige and brown adipocytes and inhibit white adipocytes in vivo, expression of markers in adipose tissues were measured after mice were treated with butein for 14 days. 6 mice were treated with 5 mg/kg of the butein through abdominal injection, and as a control, 6 mice were treated with only a solvent through abdominal injection. After 14 days, expression levels of markers for white fat and beige (brown) fat in epididymal fat, subcutaneous fat and brown fat were confirmed through real-time PCR.

Figure 6:
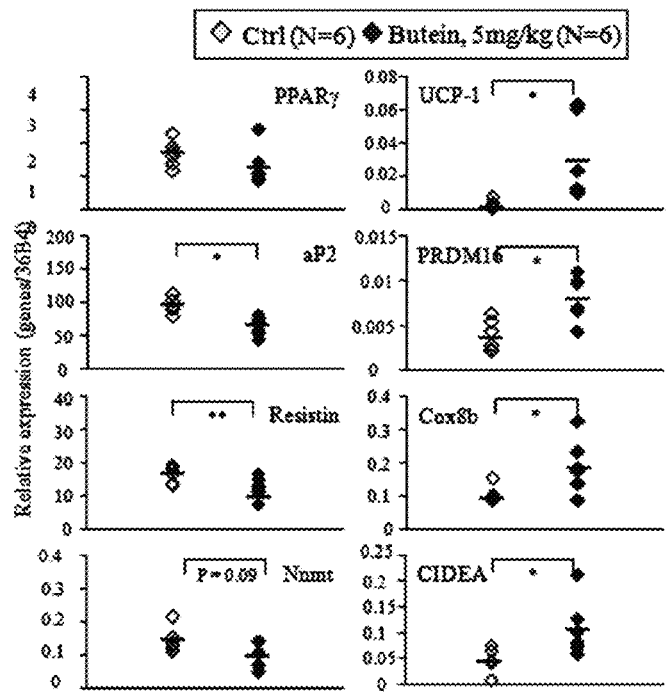
FIG. 6 shows comparison of expression levels of PPARγ and aP2 specific to adipocytes, resistin and nicotinamide N-methyltransferase (Nnmt) specific to white adipocytes, and UCP-1, PRDM16, Cox8b and Cidea specific to beige adipocytes when butein and PBS are injected into an abdominal cavity of mice in a dosage of 5 mg/kg for 14 days, and an abdominal adipose tissue, that is, epididymal fat, is isolated (Ctrl; PBS-treated group (N=6); and Butein; butein-treated group (N=6))
Figure 7:
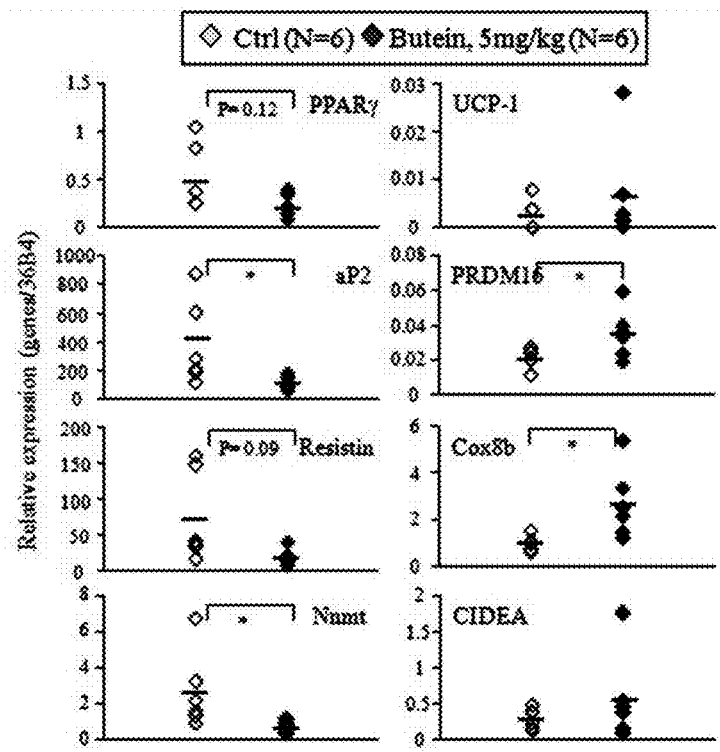
FIG. 7 shows comparison of expression levels of PPARγ and aP2 specific to adipocytes, resistin and Nnmt specific to white adipocytes, and UCP-1, PRDM16, Cox8b and Cidea specific to beige adipocytes when butein and PBS are injected into an abdominal cavity of mice in a dosage of 5 mg/kg for 14 days, and a subcutaneous adipose tissue, that is, subcutaneous fat, is isolated.
Figure 8:
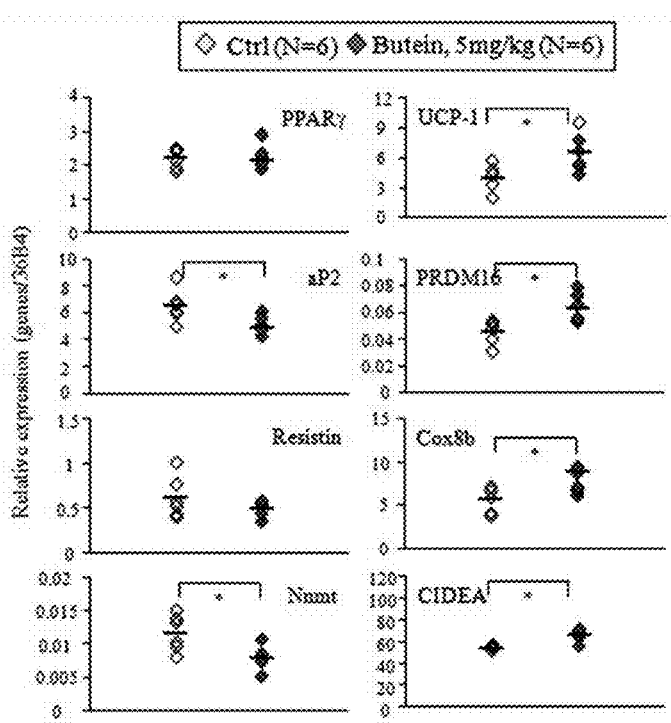
FIG. 8 shows comparison of expression levels of PPARγ and aP2 specific to adipocytes, resistin and Nnmt specific to white adipocytes, and UCP-1, PRDM16, Cox8b and Cidea specific to beige adipocytes when butein and PBS are injected into an abdominal cavity of mice in a dosage of 5 mg/kg for 14 days, and a brown adipose tissue, that is, brown fat, is isolated.
Figure 9:
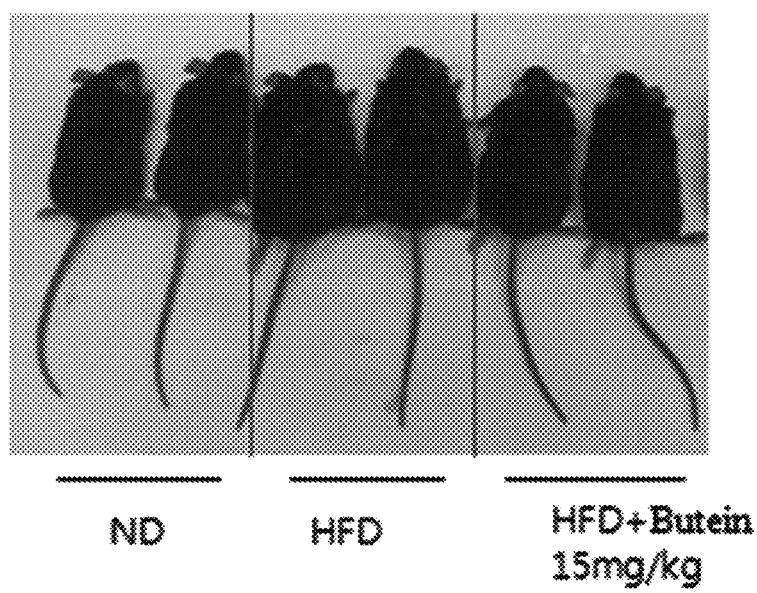
FIG. 9 is images showing apparent changes of mice for 8 weeks in an experiment in which butein is treated to C57BL/6 mice fed with HFD (ND—normal chow diet—given control (N=5); HFD—HFD obesity-induced control (n=7); and HFD+butein—group fed with HFD and treated with 15 mg/kg of butein in a route of an abdominal cavity daily (n=7))
Figure 10A:
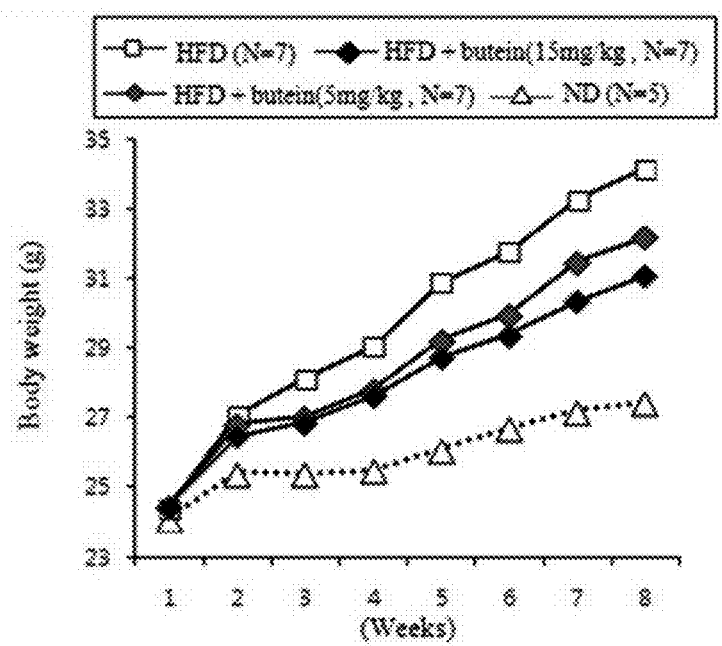
FIG. 10A is a graph showing changes in body weight for 8 weeks in an experiment in which HFD-fed C57BL/6 mice are treated with butein.
Figure 10B:
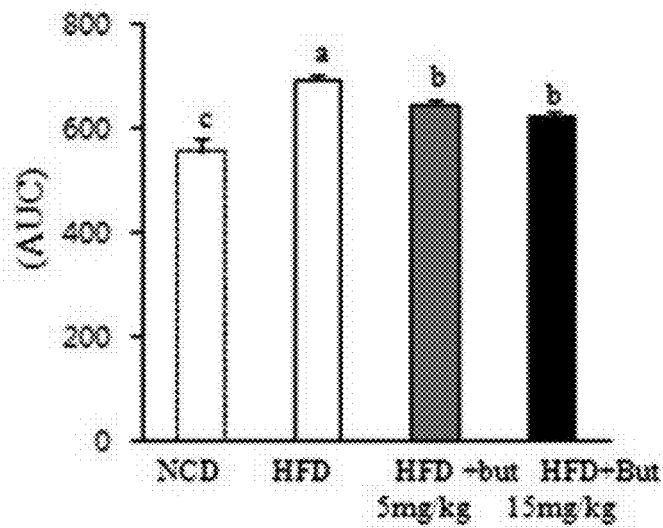
FIG. 10B shows comparison of body weight in an experiment in which HFD-fed C57BL/6 mice are treated with butein.
Figure 11:
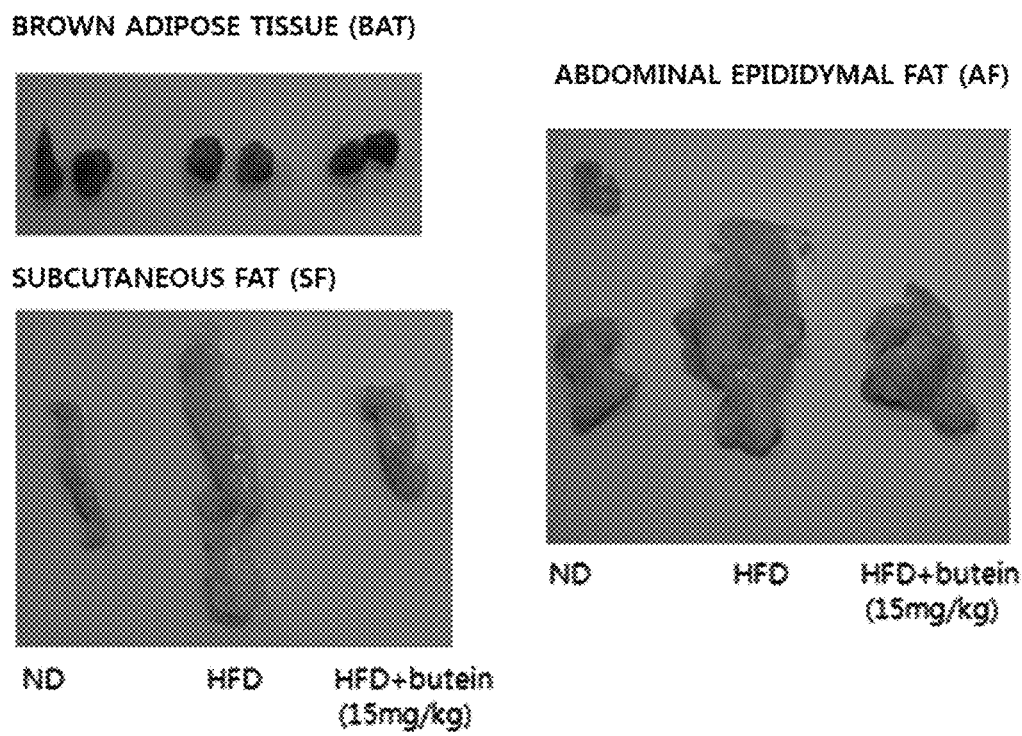
FIG. 11 is images showing comparison of sizes of brown adipose tissue (BAT), subcutaneous fat (SF) and abdominal epididymal fat (AF) of a mouse when HFD-fed C57BL/6 mice are treated with butein for 8 weeks.
Figure 12:
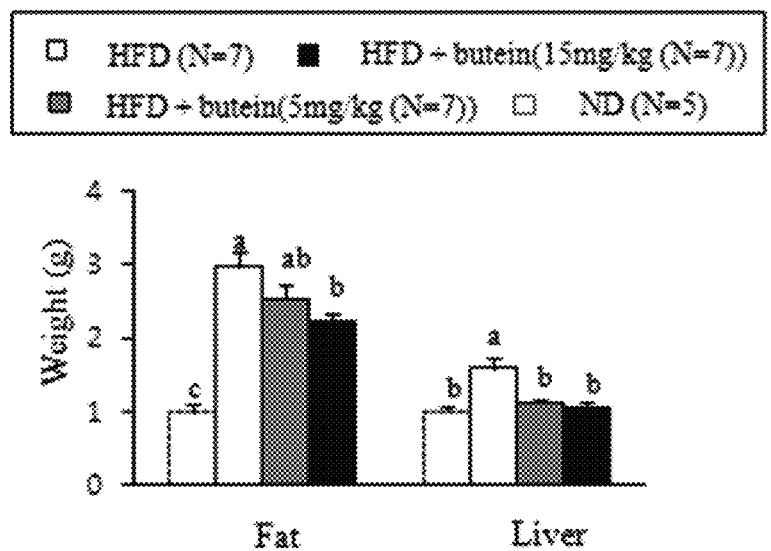
FIG. 12 is a graph showing comparison of weights of a fat pad and a liver of a mouse when HFD obesity-induced C57BL/6 mice are treated with butein for 8 weeks.
Figure 13:
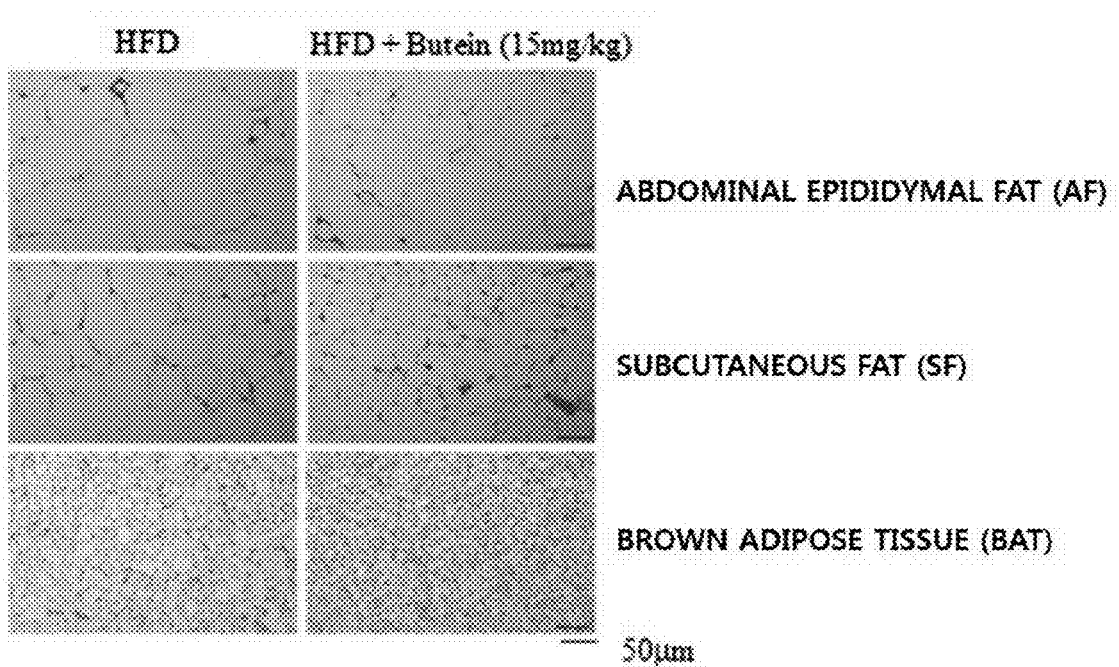
FIG. 13 is images showing comparison of AF, SF and BAT through hematoxylin and eosin (H&E) staining when HFD obesity-induced C57BL/6 mice are treated with butein for 8 weeks.
Figure 14A:
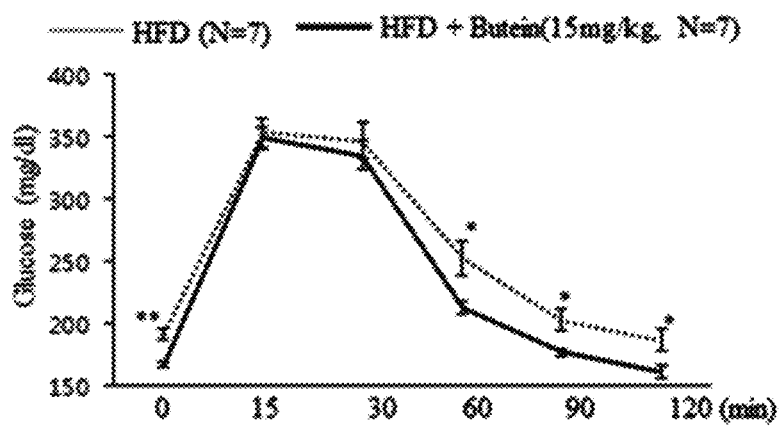
FIG. 14A shows results a glucose tolerance test for HFD obesity-induced C57BL/6 mice and mice treated with butein for 8 weeks.
Figure 14B:
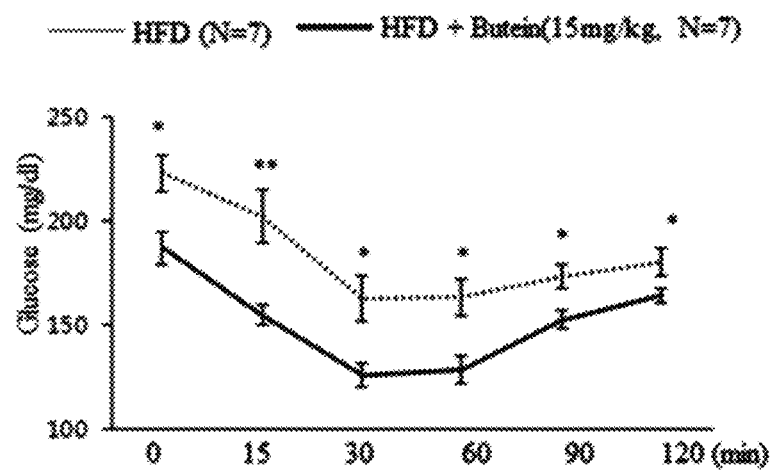
FIG. 14B shows results an insulin tolerance test for HFD obesity-induced C57BL/6 mice and mice treated with butein for 8 weeks.
Figure 15:
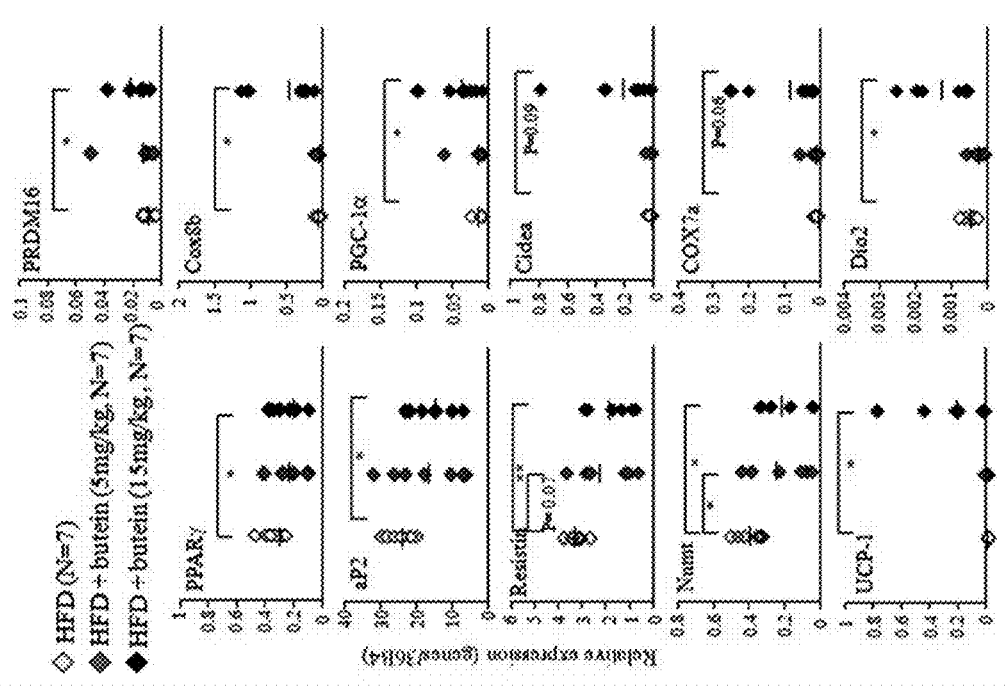
FIG. 15 shows comparison of expression levels of PPARγ and aP2 specific to adipocytes, resistin and Nnmt specific to white adipocytes, and UCP-1, PRDM16, Cox8b, PGC-1α, CIDEA, COX7a and Dio2 specific to beige adipocytes in subcutaneous adipose tissue, that is, subcutaneous fat, when obesity-induced C57BL/6 mice are treated with butein (5 and 15 mg/kg) (HFD, HFD obesity-induced control (n=7); 15, HFD+Butein (5mg/kg, N=7), group fed with HFD and treated with 5mg/kg of butein in a route of an abdominal cavity daily (n=8). HFD+Butein (15 mg/kg, N=7), group fed with HFD and treated with 15 mg/kg of butein in a route of an abdominal cavity daily (n=7)
Figure 16:
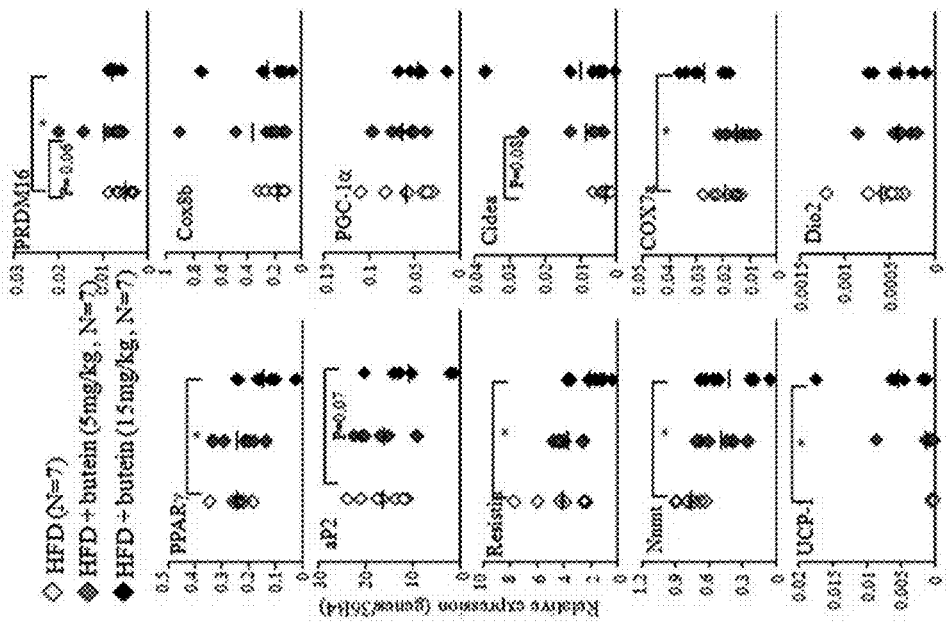
FIG. 16 shows comparison of expression levels of PPARγ and aP2 specific to adipocytes, UCP-1, PRDM16 and Cox8b specific to beige adipocytes, resistin and Nnmt specific to white adipocytes, and PGC-1α, CIDEA, COX7a and Dio2 specific to beige adipocytes in an abdominal adipose tissue, that is, epididymal fat, when obesity-induced C57BL/6 mice are treated with butein (5 and 15 mg/kg)
Figure 17:
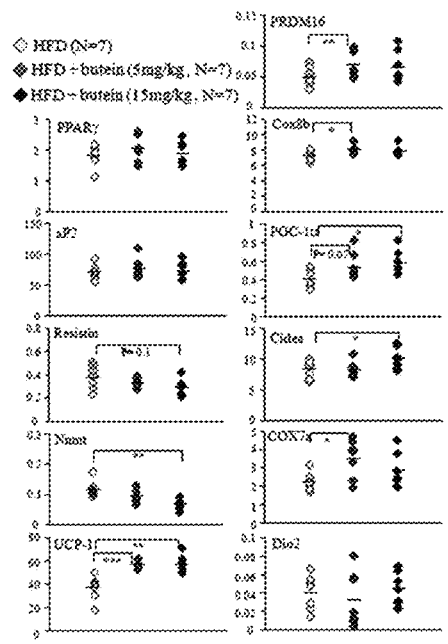
FIG. 17 shows comparison of expression levels of PPARγ and aP2 specific to adipocytes, UCP-1, PRDM16 and Cox8b specific to beige adipocytes, resistin and Nnmt specific to white adipocytes, and PGC-1α, CIDEA, COX7a and Dio2 specific to beige adipocytes in a brown adipose tissue, that is, brown fat, when obesity-induced C57BL/6 mice are treated with butein (5 and 15 mg/kg)
Figure 18:
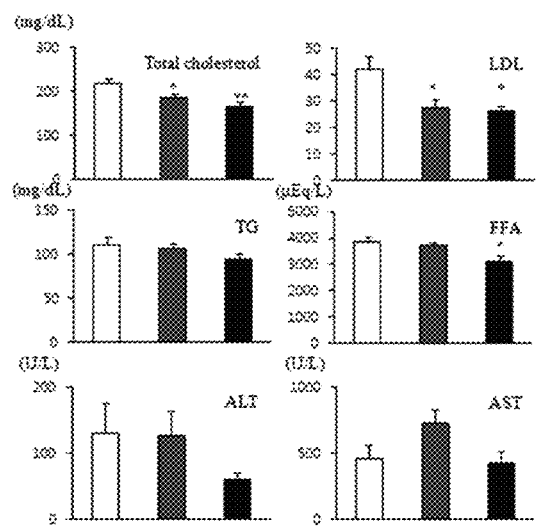
FIG. 18 shows changes in glucose in blood, neutral fat, fatty acid, LDL and cholesterol when obesity-induced C57BL/6 mice are treated with butein (5 and 15 mg/kg)
Figure 19:
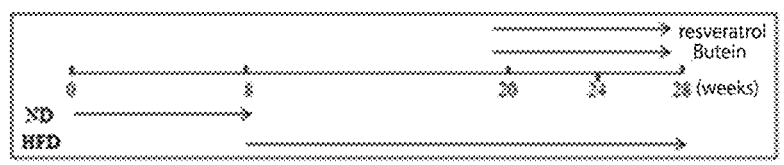
FIG. 19 is a schematic diagram illustrating an experiment for confirming an obesity effect by treating HFD obesity-induced mice with butein or resveratrol.

As shown in FIGS. 6 to 8, similar to C3H10T1/2 and T37i cells, increases in brown adipocyte markers, that is, UCP-1, PRDM16 Cox8b and Cidea, and decreases in adipocyte markers, that is, PPARγ and aP2, and white adipocyte markers, that is, resistin and Nnmt, were confirmed.

EXAMPLE 5

Confirmation of Effect of Improving Obesity in HFD Obesity-Induced Mice 5.1. Comparative Experiment with PBS-Treated Group To confirm an anti-obesity effect of butein, obesity was induced in C57BL6/J mice by HFD, and the mice were treated with butein through abdominal injection. 7-week-old mice were adjusted for 1 week, fed with HFD (60% fat, purchased from Research Diet) for 8 weeks to induce obesity, and butein was treated daily at 5 mg/kg and 15 mg/kg into two groups of mice, each group having 7 mice. As controls, a normal diet food intake group (5 mice) and a group fed with HFD and treated with PBS (7 mice) were used.

Increases in body weight during the treatment period and weights of various organs were compared, and after 8 weeks, a glucose tolerance test (GTT) and an insulin tolerance test (ITT) were performed in combination with histological and hematological analyses.

As shown in FIGS. 9 to 18, compared to the normal diet control, in the HFD control, the increased body weight and weights of adipose tissues of livers and internal organs showed a tendency to concentration-dependent decreases by treatment of butein. In addition, according to the GTT and ITT, it was confirmed that, the glucose-insulin metabolism caused by obesity was significantly improved in the group treated with 15 mg/kg of butein, and UCP-1, PRDM16, Cox8b, PGC-1α, CIDEA, COX7a and Dio2 specifically expressed in beige adipocytes were increased. In the hematological analysis, there were significant differences in glucose, cholesterol, neutral fat, HDL, LDL and a fatty acid in the group treated with a high dosage of butein.

5.2. Comparative Experiment with Resveratrol-Treated Group

To confirm an anti-obesity effect of butein, obesity was induced to C57BL6/J mice by HFD, and changes in body weight according to butein treatment were confirmed. Specifically, 7-week-old mice were adjusted for 1 week, and fed with HFD (60% fat, purchased from Research Diet) for 12 weeks to induce obesity. Afterward, 30 mg/kg of butein was treated daily into 8 of the obesity-induced mice for 8 weeks. As controls, a PBS-treated group (7 mice) and a group (8 mice) treated with resveratrol, which is known to have an effect on preventing obesity, were used.

After the 8-week treatment, increases in body weight were compared, and 8 weeks later, a GTT and a ITT were performed in combination with a hematological analysis.

Figure 20A:
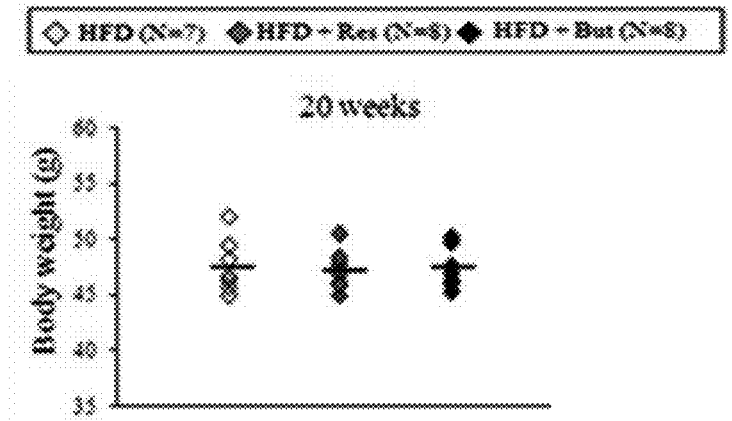
FIG. 20A shows comparison of obesity treatment effect when 20-week-old mice in which obesity is induced by HFD, are treated with butein or resveratrol.
Figure 20B:
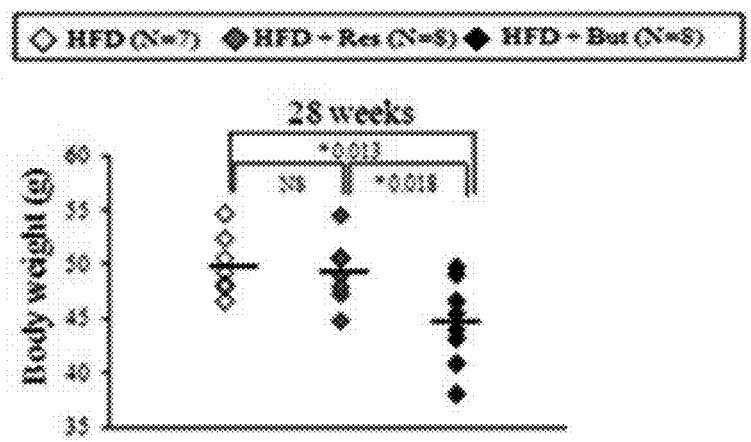
FIG. 20B shows comparison of obesity treatment effect when 28-week-old 20 mice in which obesity is induced by HFD, are treated with butein or resveratrol.
Figure 20C:
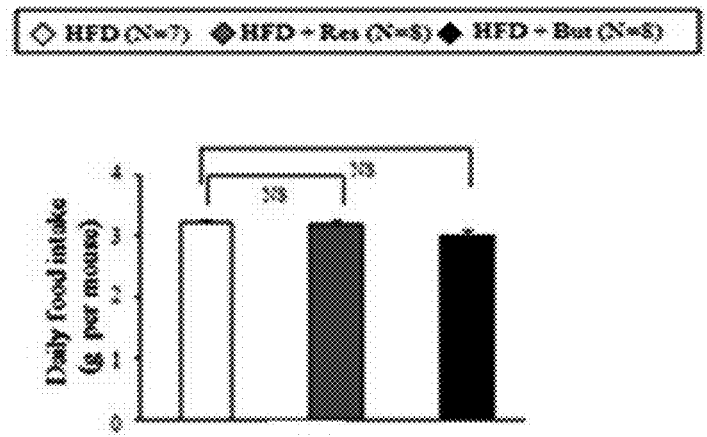
FIG. 20C shows comparison of food intake among three groups.

As shown in FIG. 20, compared to the PBS-treated group, the butein-treated group showed a tendency to decreasing a body weight by approximately 10%, and also showed a considerably excellent effect of decreasing a body weight compared to the group treated with the known anti-obesity compound, resveratrol. Specifically, compared to the control, there were no changes in body weights of the 28-week-old mice in the resveratrol-treated group. However, in the butein-treated group, a considerable decrease in body weight was confirmed, and there were no differences in food intake between three groups.

Figure 21A:
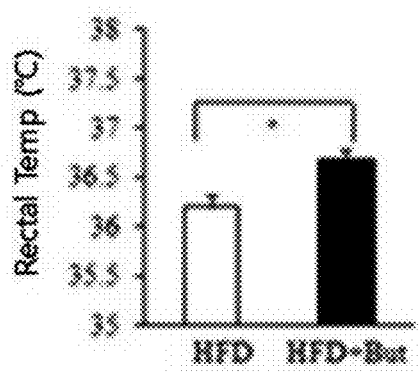
FIG. 21A is a diagram showing a change in rectal temperature caused by butein treatment to HFD obesity-induced mice.
Figure 21B:
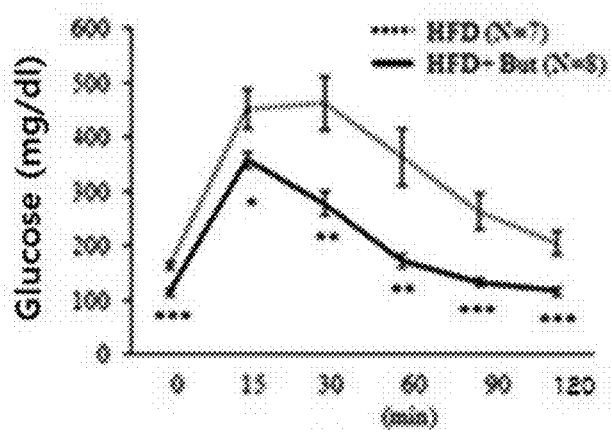
FIG. 21B is a diagram showing a result of a glucose tolerance test caused by butein treatment to HFD obesity-induced mice.
Figure 21C:
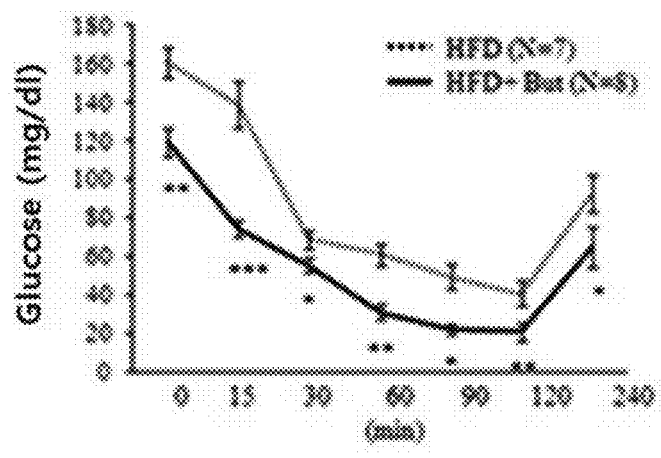
FIG. 21C is a diagram showing a result of an insulin tolerance test caused by butein treatment to HFD obesity-induced mice.

In addition, as shown in FIG. 21, a rectal temperature was increased in the butein-treated group (HFD-But), and according to the GTT and ITT, it was confirmed that the glucose-insulin metabolism caused by obesity was considerably improved (high insulin sensitivity).

EXAMPLE 6

Confirmation and Inhibition of Expression of Gene Inducing Bioactivity of Butein To confirm a gene inducing bioactivity of butein, a microarray was performed, and among these genes, PRDM4 gene increased in expression by more than approximately twice was confirmed. Particularly, to confirm induction of the bioactivity of butein, the expression of the PRDM4 gene was inhibited by small interfering RNA (siRNA), and then the differentiations into white adipocytes and beige adipocytes were compared.

Two PRDM4 siRNA sequences used in Example 6 are as follows:

PRDM4 siRNA

```
                                        (SEQ. ID. NO: 1)
    Sense 1:      5' GAAUUACGCUCAACAGAUAUU 3'

(SEQ. ID. NO: 2)
    Sense 2:      5' GAAAGUGAGCUGCUUUUCUUU'
```

Figure 22A:
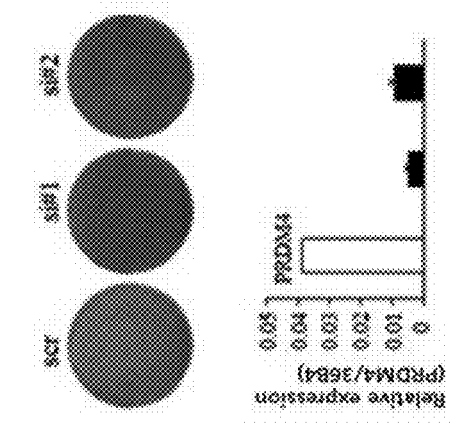
FIG. 22A shows results of confirming a degree of fat accumulation by PRDM4 siRNA (si#1 and si#2) treatment to 3T3-L1 cells using Oil Red O staining.
Figure 22B:
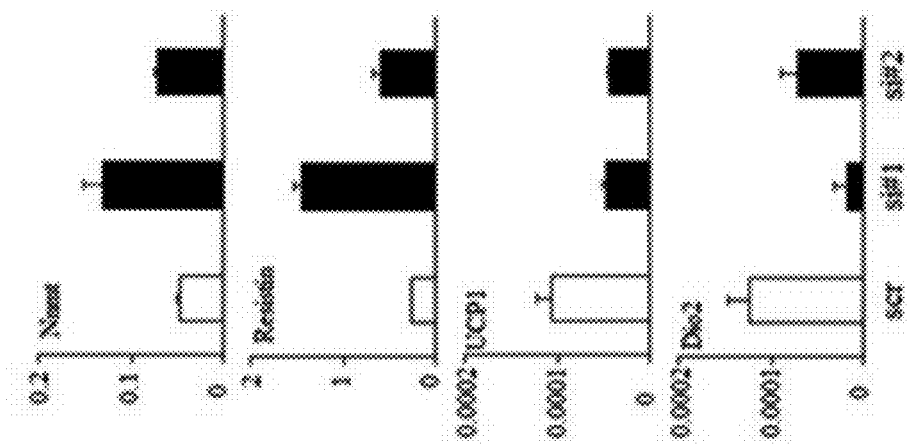
FIG. 22B shows results of confirming changes in expression of genes by PRDM4 siRNA (si#1 and si#2) treatment to C3H10T1/2 cells.
Figure 22C:
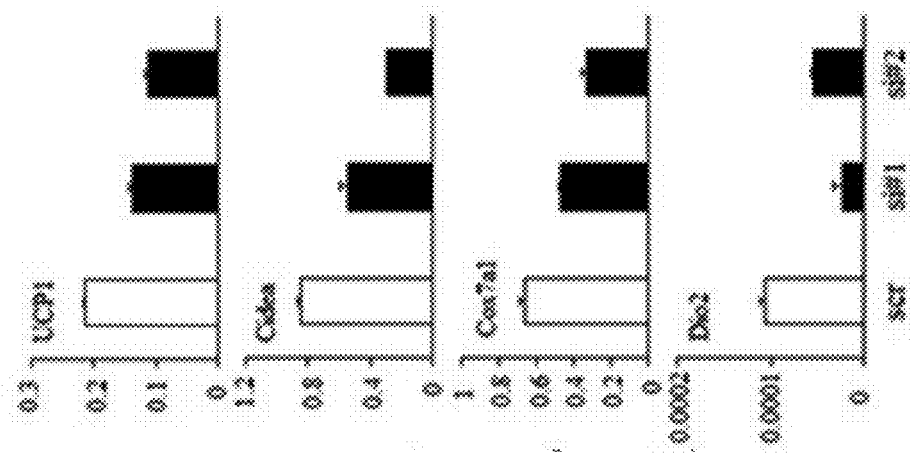
FIG. 22C shows results of confirming changes in expression of genes by PRDM4 siRNA (si#1 and si#2) treatment to t37i cells.

As shown in FIG. 22, when the differentiated adipocytes, C3H10T1/2, were treated with PRDM4 siRNA, the decrease in expression level of UCP-1 and induction and stimulation of the differentiation into white adipocytes were confirmed. Specifically, the PRDM4 siRNA increased white adipocyte markers, Nnmt and resistin, and inhibited brown adipocyte markers, UCP-1 and Dio2, in the C3H10T1/2 cells. In addition, the PRDM4 siRNA decreased expression of brown adipocyte markers, UCP-1, Cidea, Cox7a1 and Dio2, in brown adipocytes such as t37i cells. The above results show that the PRDM gene relates to the induction of brown adipocytes by butein treatment and the inhibition of white adipocytes.

EXAMPLE 7

Confirmation of Change in Body Weight through Inhibition of Expression of PRDM4 Gene To confirm functions of PRDM4 in vivo, each of PRDM4 siRNA and scrambled RNA was injected at 25 mg/kg twice a week for 6 weeks while HFD was fed. During the HFD-fed period, the increases in body weights and weights of various organs between the PRDM4 siRNA-treated group (si PRDM4) and a scrambled RNA-treated group (Scr) as a control were compared, and 6 weeks later, a GTT and an ITT were performed.

Figure 23A:
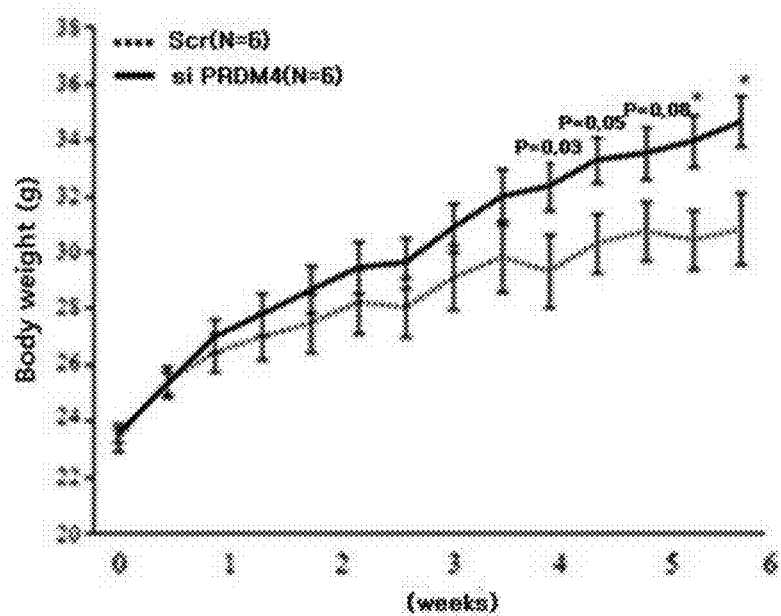
FIG. 23A shows a change in body weight when PRDM4 siRNA and scrambled RNA (scr) as a control are treated through ip injection.
Figure 23B:
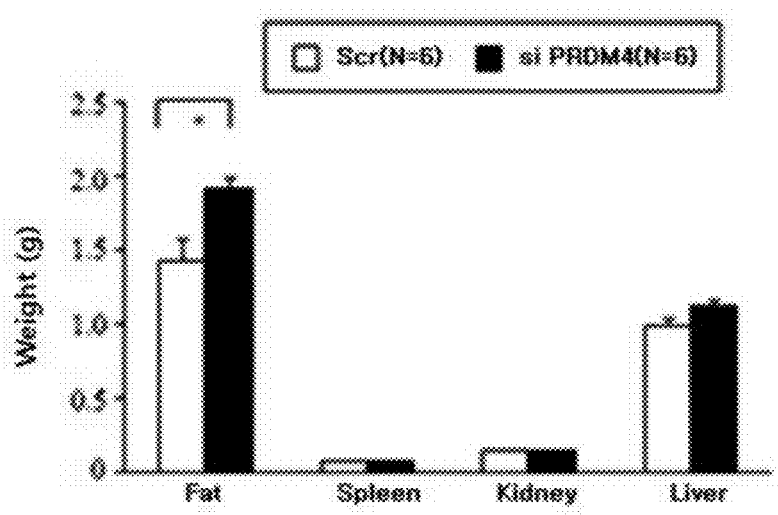
FIG. 23B shows a changes in weights of organs such as fat, a spleen, a kidney and a liver of a mouse when PRDM4 siRNA and scrambled RNA (scr) as a control are treated through ip injection.
Figure 24A:
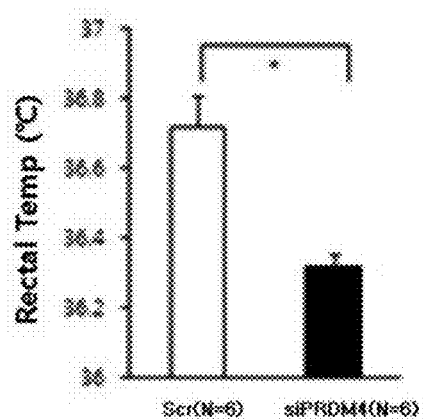
FIG. 24A is a diagram showing a change in rectal temperature of PRDM4 siRNA-treated mice.
Figure 24B:
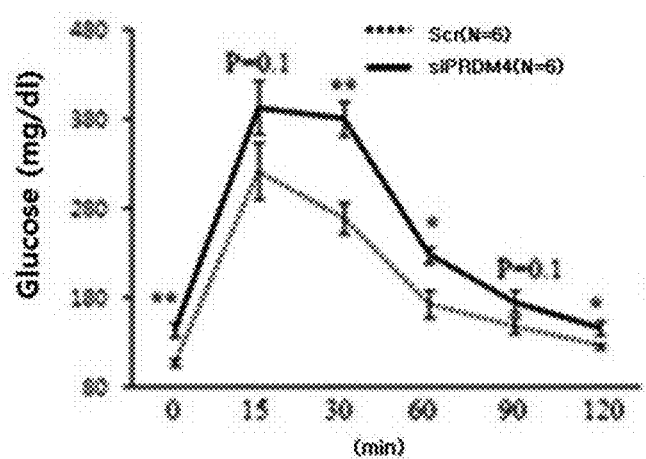
FIG. 24B is a result of a glucose tolerance test of PRDM4 siRNA-treated mice.
Figure 24C:
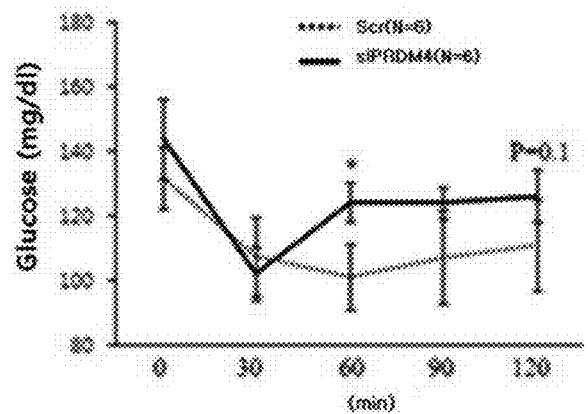
FIG. 24C is a result of an insulin tolerance test of PRDM4 siRNA-treated mice.

As shown in FIGS. 23 and 24, compared to the control, the PRDM4 siRNA-treated group showed a significant increase in body weight 4 weeks after the treatment. A weight of visceral fat (Fat) increased, and a liver tissue (Liver) was also increased. The increase in body weight shown in the PRDM4 siRNA-treated group interfered the glucose-insulin metabolism in the GTT and ITT, and the body temperature was also significantly decreased, compared to the butein-treated group.

EXAMPLE 8

Preparation of Butein and Butein Derivative

Representative examples corresponding to respective operations of manufacturing a compound are as follows. Compounds having different substituents were prepared by operations similar to the following operations, and the prepared compounds are shown in Table 1 in detail.

TABLE 1

| No. | Structure | LCMS (M + 1)+ | 1H NMR | Appearance | Pharmaceutical activity (UCP-1 expression) |
|---|---|---|---|---|---|
| 1-1 | 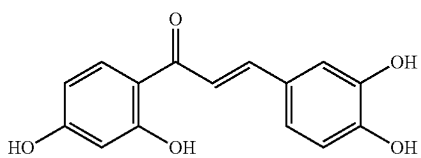 [SMILES: O=C(/C=C/c1ccc(O)c(O)c1)c1ccc(O)cc1O] | 273.1 | (MeOD) 6.28 (1H, d, J = 2.4 Hz), 6.40 (1H, dd, J = 8.8, 2.4 Hz), 6.81 (1H, d, J = 8.4 Hz), 7.10 (1H, dd, J = 8.4, 1.6 Hz), 7.17 (1H, d, J = 1.6 Hz), 7.52 (1H, d, J = 15.4 Hz), 7.71 (1H, d, J = 15.4 Hz), 7.92 (1H, d, J = 8.8 Hz) | yellow solid | 6.5 |
| 1-2 | 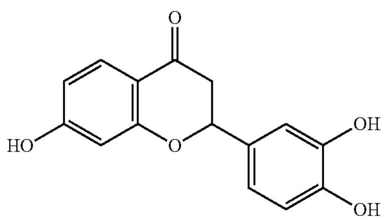 [SMILES: O=C1CC(c2ccc(O)c(O)c2)Oc2cc(O)ccc21] | 273.1 | (MeOD) 7.69 (1H, d, J = 8.7 Hz), 6.87 (1H, d, J = 1.8 Hz), 6.77 (1H, d, J = 8.2 Hz), 6.74 (1H, dd, J = 8.2, 1.8 Hz), 6.44 (1H, dd, J = 8.7, 2.2 Hz), 6.32 (1H, d, J = 2.2 Hz), 5.22 (1H, dd, J = 13.2, 2.8 Hz), 2.94 (1H, dd, J = 13.2, 17.0 Hz), 2.65 (1H, dd, J = 17.0, 2.8 Hz) | yellow solid | 0.97 |
| 1-3 | 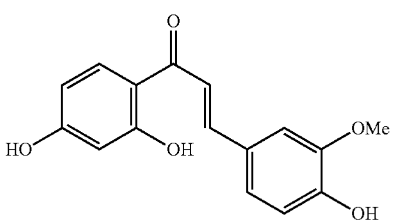 [SMILES: COc1cc(/C=C/C(=O)c2ccc(O)cc2O)ccc1O] | 287.1 | (MeOD) δ 8.05 (1H, d, J = 9.1 Hz), 7.81 (1H, d, J = 15.4 Hz), 7.67 (1H, d, 15.4 Hz), 7.40 (1H, d, J = 2.1 Hz), 7.24 (1H, dd, J = 2.1, 8.4 Hz), 6.87 (1H, d, J = 7.7 Hz), 6.44 (1H, dd, J = 2.1, 15.4 Hz), 6.31 (1H, d, J = 2.8 Hz) 3.97 (3H, s) | yellow solid | 0.98 |
| 1-4 | 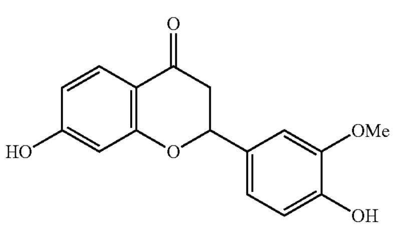 [SMILES: COc1cc(C2CC(=O)c3ccc(O)cc3O2)ccc1O] | 287.1 | (MeOD) 7.75 (1H, d, J = 8.4 Hz), 7.10 (1H, d, J = 2.1 Hz), 6.95 (1H, dd, J = 2.1, 8.4 Hz), 6.84 (1H, d, J = 8.4 Hz), 6.43 (1H, dd, J = 2.1, 8.4 Hz), 6.38 (1H, d, J = 2.1 Hz), 5.40 (1H, dd, J = 2.8, 12.6 Hz), 3.89 (3H, s), 3.10 (1H, dd, J = 6.3, 16.8 Hz), 2.72 (1H, dd, J = 2.8, 15.4 Hz) | yellow solid | 0.93 |
| 1-5 | 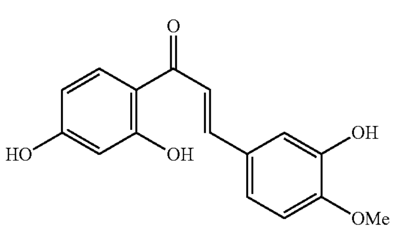 [SMILES: COc1ccc(/C=C/C(=O)c2ccc(O)cc2O)cc1O] | 287.1 | (DMSO) 13.54 (1H, s), 10.68 (1H, s), 9.14 (1H, s), 8.17 (1H, d, J = 8.8 Hz), 7.74 (1H, d, J = 15.2 Hz), 7.67 (1H, d, J = 15.2 Hz), 7.34 (1H, s), 7.31 (1H, d, J = 8.4 Hz), 7.01 (1H, d, J = 8.4 Hz), 6.40 (1H, dd, J = 1.6, 8.8 Hz), 6.27 (1H, d, J = 1.6 Hz), 3.84 (3H, s) | yellow solid | 1.14 |

TABLE 1-continued

| No. | Structure | LCMS (M + 1)+ | 1H NMR | Appearance | Pharmaceutical activity (UCP-1 expression) |
|---|---|---|---|---|---|
| 1-6 | 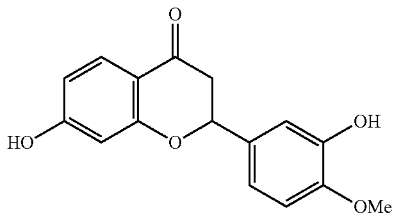 [SMILES: COc1ccc(C2CC(=O)c3ccc(O)cc3O2)cc1O] | 287.1 | (DMSO) 10.57 (1H, s), 9.08 (1H, s), 7.63 (1H, d, J = 8.8 Hz), 6.92 (2H, m), 6.87 (1H, d, J = 8.4 Hz), 6.49 (1H, dd, J = 3.2, 8.8 Hz), 6.33 (1H, d, J = 3.2 Hz), 5.43 (1H, dd, J = 2.8, 12.8 Hz), 3.76 (3H, s), 3.05 (1H, dd, J = 12.4, 16.4 Hz), 2.64 (1H, dd, J = 2.8, 16.4 Hz) | yellow solid | 1.5 |
| 1-7 | 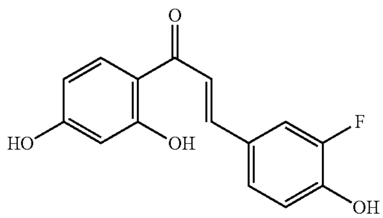 [SMILES: O=C(/C=C/c1ccc(O)c(F)c1)c1ccc(O)cc1O] | 275.1 | (MeOD) 8.01 (1H, d, J = 9.2 Hz), 7.76 (1H, d, J = 15.6 Hz), 7.67 (1H, d, J = 15.6 Hz), 7.59 (1H, dd, J = 2.0, 12.0 Hz), 7.40 (1H, dd, J = 1.2, 8.4 Hz), 6.98 (1H, t, J = 8.8 Hz), 6.44 (1H, dd, J = 2.4, 8.8 Hz), 6.31 (1H, d, 2.4 Hz) | yellow solid | 0.61 |
| 1-8 | 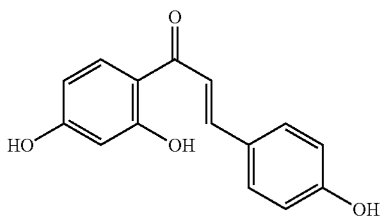 [SMILES: O=C(/C=C/c1ccc(O)cc1)c1ccc(O)cc1O] | 257.1 | (MeOD) 8.99 (1H, d, J = 9.2 Hz), 7.81 (1H, d, J = 15.2 Hz), 7.64 (3H, m), 6.86 (2H, dd, J = 3.2, 6.8 Hz), 6.43 (1H, dd, J = 2.4, 8.8 Hz), 6.31 (1H, d, J = 2.8 Hz) | yellow solid | 0.6 |
| 1-10 | 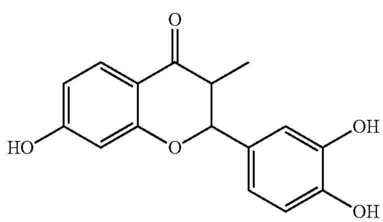 [SMILES: CC1C(=O)c2ccc(O)cc2OC1c1ccc(O)c(O)c1] | 287.1 | (MeOD) 7.72 (1H, d, J = 8.8 Hz), 6.93 (1H, s), 6.80 (2H, s), 6.50 (1H, dd, J = 2.4, 8.8 Hz), 6.32 (1H, d, J = 2.0 Hz), 2.95 (1H, m), 0.96 (3H, d, J = 6.8 Hz) | yellow solid | 0.97 |
| 1-11 | 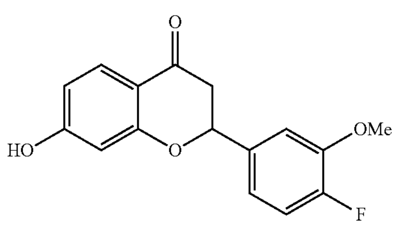 [SMILES: COc1cc(C2CC(=O)c3ccc(O)cc3O2)ccc1F] | 289.1 | (DMSO) 7.65 (1H, d, J = 8.4 Hz), 7.35 (1H, dd, J = 2.0, 8.4 Hz), 7.25 (1H, dd, J = 8.0, 11.2 Hz), 7.09 (1H, m), 6.52 (1H, dd, J = 2.0, 8.8 Hz), 6.36 (1H, d, J = 2.8 Hz), 5.48 (1H, dd, J = 2.8, 13.2 Hz), 3.86 (3H, s), 3.16 (1H, dd, J = 13.2, 16.8 Hz), 2.68 (1H, dd, J = 3.2, 16.8 Hz) | yellow solid | 10.9 |
| 1-12 | 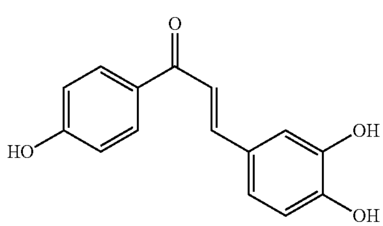 [SMILES: O=C(/C=C/c1ccc(O)c(O)c1)c1ccc(O)cc1] | 257.1 | (MeOD) 8.01 (2H, dd, J = 2.0, 6.8 Hz), 7.66 (1H, d, J = 15.6 Hz), 7.52 (1H, d, J = 15.6 Hz), 7.19 (1H, d, J = 2.4 Hz), 7.11 (1H, dd, J = 2.0, 8.4 Hz), 6.91 (2H, dd, J = 2.0, 6.8 Hz), 6.83 (1H, d, J = 8.0 Hz), | yellow solid | 5.48 |
| 1-13 | 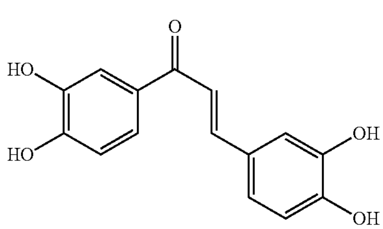 [SMILES: O=C(/C=C/c1ccc(O)c(O)c1)c1ccc(O)c(O)c1] | 273.1 | (MeOD) 7.64 (1H, d, J = 15.2 Hz), 7.56 (1H, dd, J = 2.0, 8.4 Hz), 7.51 (1H, d, J = 2.0 Hz), 7.47 (1H, d, J = 15.2 Hz), 7.18 (1H, d, J = 2.0 Hz), 7.10 (1H, dd, J = 2.0, 8.4 Hz), 6.89 (1H, d, J = 8.0 Hz), 6.82 (1H, d, J = 3.2 Hz), | yellow solid | 2.0 |

TABLE 1-continued

| No. | Structure | LCMS (M + 1)+ | 1H NMR | Appearance | Pharmaceutical activity (UCP-1 expression) |
|---|---|---|---|---|---|
| 1-14 | 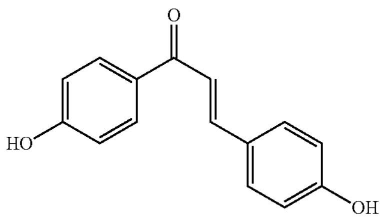 [SMILES: O=C(/C=C/c1ccc(O)cc1)c1ccc(O)cc1] | 241.1 | (MeOD) 8.02 (2H, dd, J = 2.0, 6.8 Hz),), 7.73 (1H, d, J = 15.6 Hz), 7.63 (2H, m), 7.60 (1H, d, J = 15.6 Hz), 6.92 (2H, dd, J = 2.0, 6.8 Hz), 6.86 (2H, dd, J = 2.0, 6.8 Hz) | yellow solid | 1.5 |
| 1-15 | 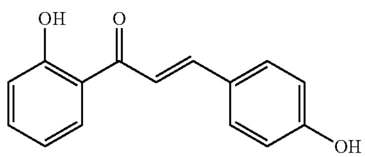 [SMILES: O=C(/C=C/c1ccc(O)cc1)c1ccccc1O] | 241.1 | (MeOD) 8.12 (1H, dd, J = 1.6, 8.0 Hz), 7.88 (1H, d, J = 15.2 Hz), 7.72 (1H, d, J = 15.2 Hz), 7.6 (2H, dd, J = 1.6, 6.8 Hz), 7.51 (1H, m), 6.98 (2H, m), 6.87 (3H, dd, J = 2.0, 6.8 Hz) | yellow solid | — |
| 1-16 | 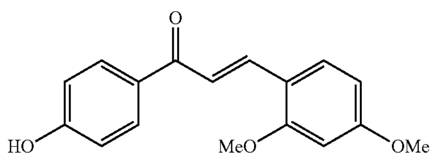 [SMILES: COc1ccc(/C=C/C(=O)c2ccc(O)cc2)c(OC)c1] | 285.1 | 1H-NMR (CD3OD): δ 8.04 (1H, d, J = 16 Hz), 7.97 (2H, dd, J = 6.8, 2.0 Hz), 7.64 (1H, d, J = 8.4 Hz), 7.62 (1H, d, J = 7.6 Hz), 6.90 (2H, dd, J = 6.8, 2.0 Hz), 6.55 (2H, d, J = 2.4 Hz), 6.52 (1H, s), 3.87 (3H, s), 3.81 (3H, s) | yellow solid | — |
| 1-17 | 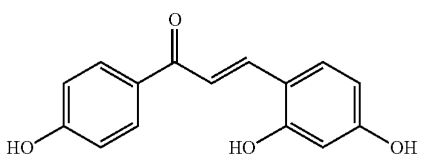 [SMILES: O=C(/C=C/c1ccc(O)cc1O)c1ccc(O)cc1] | 257.1 | 1H-NMR (CD3OD): δ 8.07 (1H, d, J = 15.6 Hz), 7.98 (2H, dd, J = 6.8, 2.0 Hz), 7.90 (2H, dd, J = 6.8, 2.0 Hz), 7.69 (1H, d, J = 15.6 Hz), 7.53 (1H, d, J = 8.4 Hz), 6.91 (2H, dd, J = 5.2, 2.8 Hz), 6.83 (1H, dd, J = 6.8, 2.0 Hz), 6.39 (1H, d, J = 3.6 Hz), 6.36 (1H, s) | yellow solid | — |
| 1-18 | 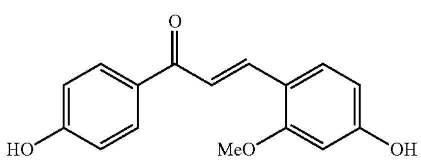 [SMILES: COc1cc(O)ccc1/C=C/C(=O)c1ccc(O)cc1] | 271.1 | 1H-NMR (CD3OD): δ 8.07 (1H, d, J = 15.6 Hz), 7.99 (2H, dd, J = 6.8, 2.0 Hz), 7.63 (2H, dd, J = 12.0, 3.6 Hz), 6.91 (2H, dd, J = 6.8, 2.0 Hz), 6.48 (1H, s), 6.46 (1H, d, J = 2.4 Hz), 3.89 (3H, s) | yellow solid | — |

8-1. Preparation of Butein

The butein compound represented by Formula 1-1 according to the present invention was prepared according to Reaction Formula 3:

[Reaction Formula 3]

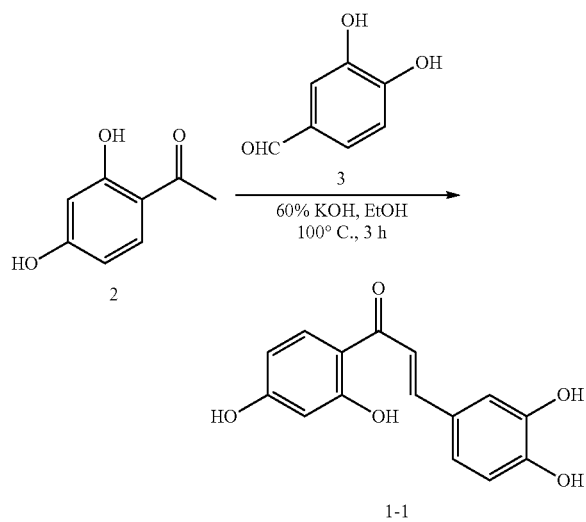

Reaction conditions for a representative example of a reaction performed in Example 8-1 are as follows: (a) reaction conditions and materials: Compound 2 (152 mg, 1 mmol) and Compound 3 (138 mg, 1 mmol) were put into a reaction container, and EtOH (0.1 ml) and a KOH aqueous solution (60% w/w, 1 ml) were added thereto to dissolve the compounds, and a temperature was increased to 100° C. to perform a reaction for 3 hours. While the temperature was slowly decreased to room temperature, HCl was dropped to reach pH 3. The reaction solution was diluted with ethyl acetate (10 ml) and washed with water (3 ml, twice), and a collected organic layer was dried with anhydrous magnesium sulfate and filtered and purified under a normal-phase column condition (ethyl acetate:nucleic acid=1:2), thereby obtaining a yellow solid, Compound 1-1 (102 mg, yield: 40%), and thus NMR data thereof is as follows: 1H, 400 MHz, DMSO-d6): δ 1H-NMR (CD3OD): δ 7.81 (1H, d, J=8.9 Hz, H-6'), 7.70 (1H, d, J=15.3 Hz, H-β), 7.40 (1H, d, J =15.3 Hz, H-α), 7.15 (1H, d,J=1.8 Hz, H-2), 7.05 (1H, dd, J=8.2, 1.8 Hz, H-6), 6.82 (1H, d, J=8.2 Hz, H-5), 6.40 (1H, dd, J=8.9, 2.4 Hz, H-5'), 6.33 (1H, d, J=2.4 Hz, H-3'), LRMs(ESI) m/z =273.1 (M+H)+.

8-2. Preparation of compound of Formula 1-2

The butein derivatives represented by Formula 1-2 according to the present invention were prepared according to Reaction Formula 4:

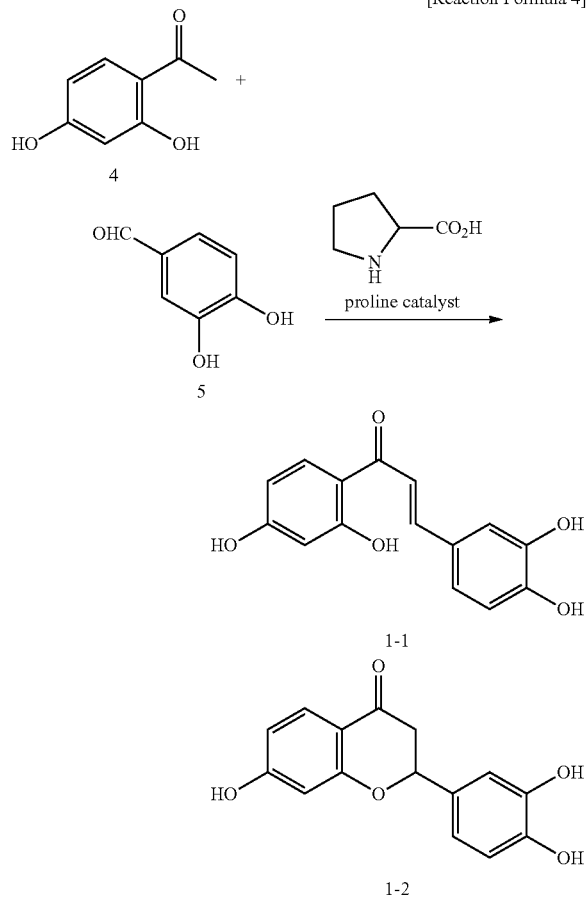

[Reaction Formula 4]

Reaction conditions for the representative reaction example performed in Example 8-2 are as follows:

(a) Reaction conditions and materials: Compound 4 (152 mg, 1 mmol) and Compound 5 (152 mg, 1 mmol) were dissolved in anhydrous methanol (5 ml), and then proline (0.5 eq, 0.5 mmol) was added. A temperature was gradually increased to 80° C., and the resulting solution was stirred for 3 days. After it was confirmed that all of Compounds 3 and 6 were consumed, the resulting product was diluted with ethyl acetate and washed with water. A collected organic layer was dried and concentrated with anhydrous magnesium sulfate, and then isolation and purification were performed through column chromatography (ethyl acetate: nucleic acid=1:2). As a result, a yellow solid, Compound 1-1 (114 mg, yield: 36%) and a yellow solid, Compound 1-2 (85 mg, yield 33%) were obtained. Here, the obtained Compound 1-1 was the same as the product of the reaction, and NMR data of Compound 1-2 is as follows: 1H NMR (DMSO-d6): 1H-NMR (CD3OD): δ 7.69 (1H, d, J=8.7 Hz, H-5), 6.87 (1H, d, J=1.8 Hz, H-2'), 6.77 (1H, d, J=8.2 Hz, H-5'), 6.74 (1H, dd, J=8.2, 1.8 Hz, H-6'), 6.44 (1H, dd, J=8.7, 2.2 Hz, H-6), 6.32 (1H, d, J=2.2 Hz, H-8), 5.22 (1H, dd, J=13.2, 2.8 Hz, H-2), 2.94 (1H, dd, J=13.2, 17.0 Hz, H-3a), 2.65 (1H, dd, J=17.0, 2.8 Hz, H-3b); Ms(ESI) m/z=273.1 (M+H)+.

EXAMPLE 9

Confirmation of Anti-Obesity Effect of Butein Derivative

To confirm an anti-obesity effect of the butein derivative, changes in expression levels of UCP-1 and PRDM4 by treatment of the butein derivative (Formulas 1-1 to 1-8 and 1-10 to 1-14) were measured. Differentiated C3H10T1/2 adipocytes were treated with the butein and the derivatives for 24 hours, and the expression levels of UCP-1 and PRDM4 were investigated using real-time PCR.

Figure 25:
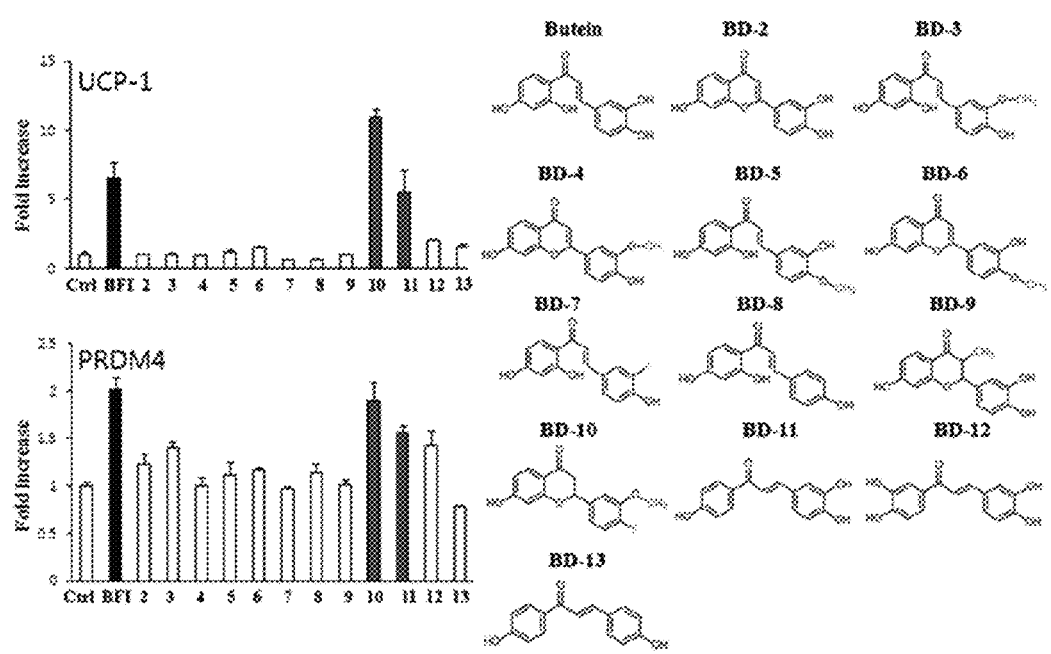
FIG. 25 shows an expression level of UCP-1 and an expression level of PRDM4 when C3H10T1/2 cells differentiating into adipocytes are treated with a butein derivative.

As a result, as shown in FIG. 25, significant increases in expression levels of UCP-1 and PRDM4 were also shown in the butein derivatives as well as the butein. Particularly, in the group treated with the butein derivatives 1-11 (BD-10) and 1-12 (BD-11), compared to the butein-treated group (BFI), it was confirmed that the expression levels of UCP-1 and PRDM4 were considerably increased.

A composition according to the present invention includes butein, a butein derivative or a pharmaceutically available salt thereof as an active ingredient, and as the concentration of the active ingredient, butein, increased, it was confirmed that expression of a beige adipocyte marker, UCP-1, increased, and therefore the composition can be used as a composition for inducing differentiation into beige adipocytes, and is also expected to be used to prevent or treat obesity or a metabolic disease.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of inhibiting obesity, comprising:
administering a composition comprising butein, a butein derivative, or a pharmaceutically available salt thereof, as an active ingredient to an individual in need of obesity inhibition,
wherein the butein derivative is prepared by reacting Compound C with Compound D in the presence of a proline catalyst:

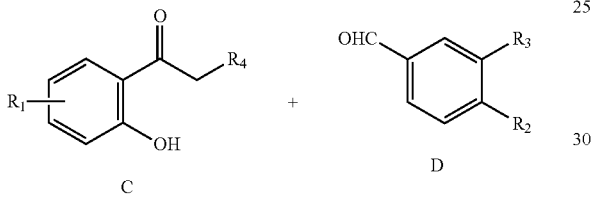

where $R_1$ is hydrogen, halogen, linear or branched C1-C6 alkyl, linear or branched C2-C6 alkenyl, linear or branched C2-C6 alkynyl, OH, $OR_5$, or $O(CO)R_5$, in which $R_5$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S,
where $R_2$ and $R_3$ are identical to or different from each other, each being hydrogen, halogen, linear or branched C1-C6 alkyl, linear or branched C2-C6 alkenyl, linear or branched C2-C6alkynyl, OH, $OR_6$, or $O(CO)R_6$, in which $R_6$ is linear or branched C1-C6 alkyl, linear or branched C2-C6 alkenyl, linear or branched C2-C6 alkynyl, C2-C6 aryl, C3-C6 cycloalkyl, or C3-C10 hetercyclyl containing at least one heteroatom selected from the group consisting of N, O, and S, and
where $R_4$ is hydrogen or linear or branched C1-C6 alkyl; or
wherein the butein derivative is prepared by reacting Compound E with Compound F in the presence of a base catalyst:

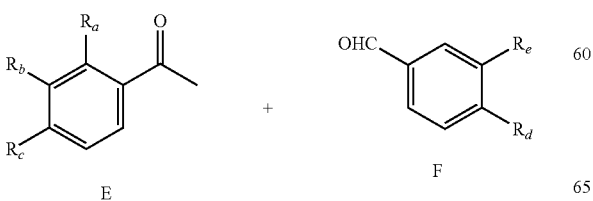

where $R_a$, $R_b$, and $R_c$ are identical to or different from each other, each being hydrogen, halogen, linear or branched C1-C6 alkyl, linear or branched C2-C6 alkenyl, linear or branched C2-C6 alkynyl, OH, $OR_g$, or $O(CO)R_g$, in which $R_g$ is linear or branched C1C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, and
where $R_d$ and $R_e$ are identical to or different from each other, each being hydrogen, halogen, linear or branched C1-C6 alkyl, linear or branched C2-C6 alkenyl, linear or branched C2-C6 alkynyl, OH, $OR_f$, or $O(CO)R_f$, in which $R_f$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S.

2. The method of claim 1, wherein the administering increases an activity of brown adipocytes.

3. The method of claim 1, wherein the administering increases expression of uncoupling protein-1 (UCP-1).

4. The method of claim 1, wherein the administering increases expression of a PRDM4 gene.

5. A method of inhibiting obesity, comprising:
administering a composition comprising a compound represented by Formula 1 or a compound represented by Formula 2, or a pharmaceutically available salt thereof as an active ingredient, to an individual in need of obesity inhibition:

[Formula 1]

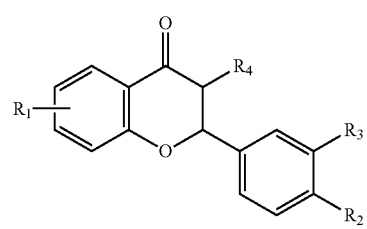

where $R_1$ is hydrogen, halogen, linear or branched C1-C6 alkyl, linear or branched C2-C6 alkenyl, linear or branched C2-C6 alkynyl, OH, $OR_5$, or $O(CO)R_5$, in which $R_5$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S,
where $R_2$ and $R_3$ are identical to or different from each other, each being hydrogen, halogen, linear or branched C1-C6 alkyl, linear or branched C2-C6 alkenyl, linear or branched C2-C6 alkynyl, OH, $OR_6$, or $O(CO)R_6$, in which $R_6$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, and $R_4$ is hydrogen or linear or branched C1-C6 alkyl;

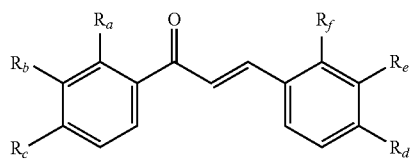

[Formula 2]

where $R_a$, $R_b$, and $R_c$ are identical to or different from each other, each being hydrogen, halogen, linear or branched C1-C6 alkyl, linear or branched C2-C6 alkenyl, linear or branched C2-C6 alkynyl, OH, $OR_g$, or $O(CO)R_g$, in which $R_g$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, where $R_d$, $R_e$, and $R_f$ are identical to or different from each other, each being hydrogen, halogen, linear or branched C1-C6 alkyl, linear or branched C2-C6 alkenyl, linear or branched C2-C6 alkynyl, OH, $OR_h$, or $O(CO)R_h$, in which $R_h$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S.

6. The method of claim 5, wherein the compound is represented by Formula 1:

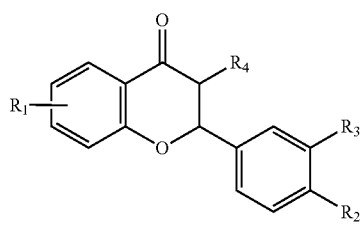

[Formula 1]

where $R_1$ is OH or C1-C6 alkyl,
$R_2$ is OH, halogen or C1-C6 alkoxy,
$R_3$ is OH or C1-C6 alkoxy,
and $R_4$ is hydrogen or C1-C6 alkyl.

7. The method of claim 5, wherein the compound is represented by Formula 2:

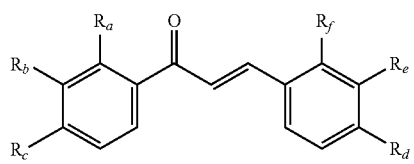

[Formula 2]

where $R_a$, $R_b$, and $R_c$ are identical to or different from each other, each being hydrogen or OH,
$R_d$ is OH, or C1-C6 alkoxy,
$R_e$ is hydrogen, OH, halogen, or C1-C6 alkoxy,
and $R_f$ is hydrogen, OH, or C1-C6 alkoxy.

8. The method of claim 5, wherein the compound is selected from the group consisting of
2-(3,4-dihydroxyphenyl)-7-hydroxychroman-4-one;
(E)-1-(2,4-dihydroxyphenyl)-3-(4-hydroxy-3-methoxyphenyl)prop-2-en-1-one;
7-hydroxy-2-(4-hydroxy-3-methoxyphenyl)chroman-4-one;
(E)-1-(2,4-dihydroxyphenyl)-3-(3-hydroxy-4-methoxyphenyl)prop-2-en-1-one;
7-hydroxy-2-(3-hydroxy-4-methoxyphenyl)chroman-4-one;
(E)-1-(2,4-dihydroxyphenyl)-3-(3-fluoro-4-hydroxyphenyl)prop-2-en-1-one;
(E)-1-(2,4-dihydroxyphenyl)-3-(4-hydroxyphenyl)prop-2-en-1-one;
2-(3,4-dihydroxyphenyl)-7-hydroxy-3-methylchroman-4-one;
2-(4-fluoro-3-methoxyphenyl)-7-hydroxychroman-4-one;
(E)-3-(3,4-dihydroxyphenyl)-1-(4-hydroxyphenyl)prop-2-en-1-one;
(E)-1,3-bis(3,4-dihydroxyphenyl)prop-2-en-1-one;
(E)-1,3-bis(4-hydroxyphenyl)prop-2-en-1-one;
(E)-1-(2-hydroxyphenyl)-3-(4-hydroxyphenyl)prop-2-en-1-one;
(E)-3-(2,4-dimethoxyphenyl)-1-(4-hydroxyphenyl)prop-2-en-1-one;
(E)-3-(2,4-dihydroxyphenyl)-1-(4-hydroxyphenyl)prop-2-en-1-one, and
(E)-3-(4-hydroxy-2-methoxyphenyl)-1-(4-hydroxyphenyl)prop-2-en-1-one.

9. The method of claim 5, wherein the administering increases an activity of brown adipocytes.

10. The method of claim 5, wherein the administering increases expression of uncoupling protein-1 (UCP-1).

11. The method of claim 5, wherein the administering increases expression of a PRDM4 gene.

12. A method of managing obesity, comprising:
administering a composition comprising a compound represented by Formula 1 or a compound represented by Formula 2, or a pharmaceutically available salt thereof as an active ingredient, to an individual in need of obesity management:

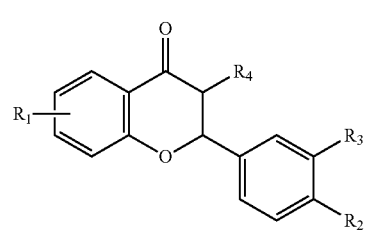

[Formula 1]

where $R_1$ is hydrogen, halogen, linear or branched C1-C6 alkyl, linear or branched C2-C6 alkenyl, linear or branched C2-C6 alkynyl, OH, $OR_5$, or $O(CO)R_5$, in which $R_5$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, where $R_2$ and $R_3$ are identical to or different from each other, each being hydrogen, halogen, linear or branched C1-C6 alkyl, linear or branched C2-C6 alkenyl, linear or branched C2-C6 alkynyl, OH, $OR_6$, or $O(CO)R_6$, in which $R_6$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, and $R_4$ is hydrogen or linear or branched C1-C6 alkyl;

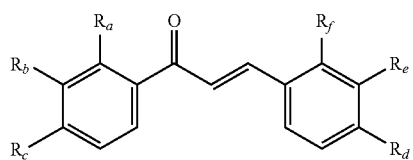

[Formula 2]

where $R_a$, $R_b$, and $R_c$ are identical to or different from each other, each being hydrogen, halogen, linear or branched C1-C6 alkyl, linear or branched C2-C6 alkenyl, linear or branched C2-C6 alkynyl, OH, $OR_g$, or $O(CO)R_g$, in which $R_g$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S, where $R_d$, $R_e$, and $R_f$ are identical to or different from each other, each being hydrogen, halogen, linear or branched C1-C6 alkyl, linear or branched C2-C6 alkenyl, linear or branched C2-C6 alkynyl, OH, $OR_h$, or $O(CO)R_h$, in which $R_h$ is linear or branched C1-C6 alkyl, linear or branched C2-C6 alkenyl, linear or branched C2-C6 alkynyl, C2-C6 aryl, C3-C6 cycloalkyl, or C3-C10 heterocyclyl containing at least one heteroatom selected from the group consisting of N, O, and S.

13. The method of claim 12, wherein the compound is represented by Formula 1:

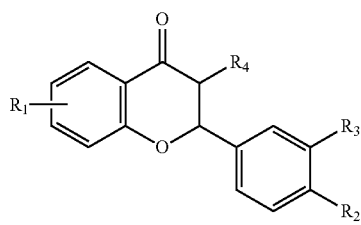

[Formula 1]

where $R_1$ is OH or C1-C6 alkyl,
$R_2$ is OH, halogen or C1-C6 alkoxy,
$R_3$ is OH or C1-C6 alkoxy,
and $R_4$ is hydrogen or C1-C6 alkyl.

14. The method of claim 12, wherein the compound is represented by Formula 2:

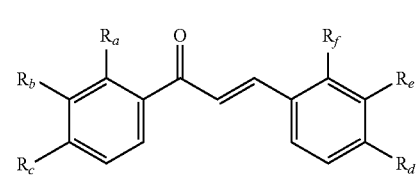

[Formula 2]

where $R_a$, $R_b$, and $R_c$ are identical to or different from each other, each being hydrogen or OH,
$R_d$ is OH, or C1-C6 alkoxy,
$R_e$ is hydrogen, OH, halogen, or C1-C6 alkoxy,
and $R_f$ is hydrogen, OH, or C1-C6 alkoxy.

15. The method of claim 12, wherein the compound is selected from the group consisting of
2-(3,4-dihydroxyphenyl)-7-hydroxychroman-4-one;
(E)-1-(2,4-dihydroxyphenyl)-3-(4-hydroxy-3-methoxyphenyl)prop-2-en-1-one;
7-hydroxy-2-(4-hydroxy-3-methoxyphenyl)chroman-4-one;
(E)-1-(2,4-dihydroxyphenyl)-3-(3-hydroxy-4-methoxyphenyl)prop-2-en-1-one;
7-hydroxy-2-(3-hydroxy-4-methoxyphenyl)chroman-4-one;
(E)-1-(2,4-dihydroxyphenyl)-3-(3-fluoro-4-hydroxyphenyl)prop-2-en-1-one;
(E)-1-(2,4-dihydroxyphenyl)-3-(4-hydroxyphenyl)prop-2-en-1-one;
2-(3,4-dihydroxyphenyl)-7-hydroxy-3-methylchroman-4-one;
2-(4-fluoro-3-methoxyphenyl)-7-hydroxychroman-4-one;
(E)-3-(3,4-dihydroxyphenyl)-1-(4-hydroxyphenyl)prop-2-en-1-one;
(E)-1,3-bis(3,4-dihydroxyphenyl)prop-2-en-1-one;
(E)-1,3-bis(4-hydroxyphenyl)prop-2-en-1-one;
(E)-1-(2-hydroxyphenyl)-3-(4-hydroxyphenyl)prop-2-en-1one;
(E)-3-(2,4-dimethoxyphenyl)-1-(4-hydroxyphenyl)prop-2-en-1-one;
(E)-3-(2,4-dihydroxyphenyl)-1-(4-hydroxyphenyl)prop-2-en-1-one, and
(E)-3-(4-hydroxy-2-methoxyphenyl)-1-(4-hydroxyphenyl)prop-2-en-1-one.

16. The method of claim 12, wherein the administering increases an activity of brown adipocytes.

17. The method of claim 12, wherein the administering increases expression of uncoupling protein-1 (UCP-1).

18. The method of claim 12, wherein the administering increases expression of a PRDM4 gene.

* * * * *